United States Patent
Bhatia et al.

(10) Patent No.: US 8,906,684 B2
(45) Date of Patent: Dec. 9, 2014

(54) THREE DIMENSIONAL CELL PATTERNED BIOPOLYMER SCAFFOLDS AND METHODS OF MAKING THE SAME

(75) Inventors: Sangeeta N. Bhatia, Lexington, MA (US); Valerie Liu Tsang, Oceanside, CA (US); Dirk R. Albrecht, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 543 days.

(21) Appl. No.: 11/035,394

(22) Filed: Jan. 12, 2005

(65) Prior Publication Data

US 2005/0169962 A1 Aug. 4, 2005

Related U.S. Application Data

(63) Continuation-in-part of application No. PCT/US03/21782, filed on Jul. 14, 2003.

(60) Provisional application No. 60/395,872, filed on Jul. 12, 2002, provisional application No. 60/401,854, filed on Aug. 7, 2002.

(51) Int. Cl.
| | |
|---|---|
| *C12N 5/00* | (2006.01) |
| *G01N 33/543* | (2006.01) |
| *G01N 33/50* | (2006.01) |
| *C12P 21/00* | (2006.01) |
| *G03F 7/00* | (2006.01) |

(52) U.S. Cl.
CPC ........ *G01N 33/502* (2013.01); *G01N 33/54353* (2013.01); *G01N 33/5067* (2013.01); *G01N 33/5008* (2013.01); *C12P 21/00* (2013.01); *G03F 7/00* (2013.01); *G01N 33/5044* (2013.01)
USPC ............ 435/382; 435/325; 435/373; 435/395

(58) Field of Classification Search
USPC .......................................... 435/395, 402, 373
See application file for complete search history.

(56) References Cited

U.S. PATENT DOCUMENTS

| | | | |
|---|---|---|---|
| 5,443,950 A | 8/1995 | Naughton | |
| 5,486,546 A | 1/1996 | Mathiesen | |
| 5,514,378 A | 5/1996 | Mikos | |
| 5,776,748 A | 7/1998 | Singhvi | |
| 6,160,084 A | 12/2000 | Langer | |
| 6,197,575 B1 | 3/2001 | Griffith et al. | |
| 6,203,573 B1 | 3/2001 | Walter | |
| 6,337,198 B1 | 1/2002 | Levene | |
| 6,379,962 B1 | 4/2002 | Holy | |
| 2002/0076690 A1* | 6/2002 | Miles et al. | 435/5 |
| 2003/0175824 A1* | 9/2003 | Pishko et al. | 435/7.2 |

FOREIGN PATENT DOCUMENTS

WO WO 0140786 A1 * 6/2001

OTHER PUBLICATIONS

Matsue, T et al. Rapid micropatterning of living cells by repulsive dielectrophoretic force. Electrochimica Acta. 1997. 42(20-22): 3251-3256.*
Elisseeff, J et al. Photoencapsulation of chondrocytes in poly(ethylene oxide)-based semi-interpenetrating networks. 2000. 51(2): 165-171.*
Alp, B et al. Formation of artificial, structured microbial consortia (ASMC) by dielectrophoresis. Enzyme and Microbial Technology. 2002. 31: 35-43. Published online Mar. 20, 2002.*
Koh, W et al. Poly(ethylene glycol) hydrogel microstructures encapsulating living cells. Langmuir. 2002. 18: 2459-2462. Published on web Feb. 21, 2002.*
Suehiro, J et al. The dielectrophoretic movement and positioning of a biological cell using a three-dimensional grid electrode system. J. Phys. D: Appl. Phys. 1998. 31: 3298-3305.*
Cruise, GM et al. A sensitivity study of the key parameters in the interfacial photopolymerization of poly(ethylene glycol) diacrylate upon porcine islets. Biotechnology and Bioengineering. 1998. 57(6): 655-665.*
Tsutsui, H et al. Efficient dielectrophoretic patterning of embryonic stem cells in energy landscapes defined by hydrogel geometries. Annals of Biomedical Engineering. 2010. 38(12): 3777-3788.*
Bhatia et al., "Micropatterning Cells in Tissue Engineering" Methods in Molecular Medicine, vol. 18, pp. 349-363 (1998).
Bhatia et al. "Controlling Cell Interactions by Micropatterning in Co-Cultures: Hepatocytes and 3T3 Fibroblasts" Journal of Biomedical Research, vol. 34, 189-199 (1997).
Allen, Jared W. et al., "Engineering Liver Therapies for the Future," Tissue Engineering, vol. 8(5):725-737 (2002).
Allen, Jared W. et al., "Improving the next generation of bioartificial liver devices," Seminars in Cell & Developmental Biology, vol. 13:447-454 (2002).
Beebe, David J. et al., "Functional hydrogel structures for autonomous flow control inside microfluidic channels," Nature, vol. 404:588-590 (2000).

(Continued)

*Primary Examiner* — Lora E Barnhart Driscoll
*Assistant Examiner* — Susan E Fernandez
(74) *Attorney, Agent, or Firm* — Nelson Mullins Riley & Scarborough LLP; Amy E. Mandragouras, Esq.; Christopher L. Frank

(57) ABSTRACT

Provided are methods of the production of patterned 3-dimensional biopolymer scaffolds containing living cells. The methods include selective photopolymerization of biopolymers to create patterned structures and the patterning of cells within relatively homogenous slabs of biopolymer using dielectrophoresis. Also provided are patterned 3-dimensional biopolymer scaffolds generated by the methods and their use.

11 Claims, 10 Drawing Sheets

(56) References Cited

OTHER PUBLICATIONS

Bhatia, S.N. et al., "Effect of cell-cell interactions in preservation of cellular phenotype: cocultivation of hepatocytes and nonparenchymal cells," FASEB J., vol. 13:1883-1900 (1999).

Elisseeff, J. et al., "Transdermal photopolymerization for minimally invasive implantation," Proc. Natl. Acad. Sci. USA, vol. 96:3104-3107 (1999).

Gobin, Andrea S. et al., "Cell migration through defined, synthetic ECM analogs," The FASEB Journal, vol. 16:751-753 (2002).

Griffith, Linda G. et al., "In Vitro Organogenesis of Liver Tissue," Annals of the New York Academy of Sciences, vol. 831:382-397 (1997).

Lee, Kuen Yong et al., "Controlled growth factor release from synthetic extracellular matrices," Nature, vol. 408:998-1000 (2000).

Ma, Peter X. et al., "Microtubular architecture of biodegradable polymer scaffolds," J. Biomed. Mater. Res., vol. 56:469-477 (2001).

Mooney, David J. et al., "Long-term engraftment of hepatocytes transplanted on biodegradable polymer sponges," J. Biomed. Mater. Res., vol. 37:413-420 (1997).

Ozkan, M. et al., "Electro-Optical Platform for the Manipulation of Live Cells," Langmuir, vol. 19(5):1532-1538 (2003).

Ozkan, Mihrimah et al., "Optical Addressing of Polymer Beads in Microdevices," Sensors and Materials, vol. 14 (4):189-197 (2002).

Park, Ann et al., "Integration of surface modification and 3D fabrication techniques to prepare patterned poly(L-lactide) substrates allowing regionally selective cell adhesion," J. Biomater. Sci. Polymer Adn., vol. 9(2):89-110 (1998).

Sawhney, Amarpreet S. et al., "Interfacial photopolymerization of poly(ethylene glycol)-based hydrogels upon alginate-poly(l-lysine) microcapsules for enhanced biocompatibility," Biomaterials, vol. 14(13):1008-1016 (1993).

Tranquillo, R.T. et al., "Magnetically oriented tissue-equivalent tubes: application to a circumferentially oriented media-equivalent," Biomaterials, vol. 17:349-357 (1996).

Wald, Heidi L. et al., "Cell seeding in porous transplantation devices," Biomaterials, vol. 14(4):270-278 (1993).

Ward, Jennifer H. et al., "Micropatterning of biomedical polymer surfaces by novel UV polymerization techniques," J. Biomed. Mater. Res., vol. 56:351-360 (2001).

Albrecht, Dirk R. et al., "Dielectrophoretic Cell Patterning Within tissue Engineering Scaffolds," Proceedings of the Second Joint EMBS/BMES Conference, pp. 1708-1709 (2002).

Albrecht, Dirk R. et al., "Geometric and Material Determinants of Patterning Efficiency by Dielectrophoresis," Biophysical Journal, vol. 87:2131-2147 (2004).

Albrecht, Dirk R. et al., "Multiphase electropatterning of cells and biomaterials," Lab Chip, vol. 7:702-709 (2007).

Albrecht, Dirk R. et al., "Photo- and electopatterning of hydrogel-encapsulated living cell arrays," The Royal Society of Chemistry, vol. 5:111-118 (2005).

Gray, Darren S. et al., "Dielectrophoretic registration of living cells to a microelectrode array," Biosensors and Bioelectronics, vol. 19(7):771-780 (2004).

Koh, Won-Gun et al., "Control of Mammalian Cell and Bacteria Adhesion on Substrates Micropatterned with Poly (ethylene glycol) Hydrogels," Biomedical Microdevices, vol. 5(1):11-19 (2003).

Lin, Ruei-Zeng et al., "Dielectrophoresis based-cell patterning for tissue engineering," Biotechnol. J., vol. 1:949-957 (2006).

Liu, Valerie A. et al., "Three-Dimensional Photopatterning of Hydrogels Containing Living Cells," Biomedical Microdevices, vol. 4(4):257-266 (2002).

Tsang, Valerie Liu et al., "Three-dimensional tissue fabrication," Advanced Drug Delivery Reviews, vol. 56:1635-1647 (2004).

* cited by examiner

THREE DIMENSIONAL CELL PATTERNED BIOPOLYMER SCAFFOLDS AND METHODS OF MAKING THE SAME

RELATED APPLICATIONS

This application is a continuation-in-part of International PCT application PCT/US2003/021782 filed Jul. 14, 2003. This application also claims the benefit of priority of U.S. provisional patent application Ser. No. 60/395,872 filed Jul. 12, 2002 and Ser. No. 60/401,854 filed Aug. 7, 2002. The above-referenced applications are incorporated herein by reference in their entirety.

FIELD

The invention relates to the field of tissue engineering. More specifically, it relates to 3-dimensional hydrogel scaffolds for the growth and maintenance of cells in culture for use in simulated organ and tissue function, the study of cell-cell and cell-matrix interactions and the development and testing of bioactive compounds.

BACKGROUND

Tissue engineering seeks to repair, replace or restore tissue function, typically by combining biomaterials and living cells. Control of polymer scaffold architecture is of fundamental importance in tissue engineering A wide variety of techniques for controlling the architecture of biomaterials are already available for relatively large feature sizes on the order of millimeters to centimeters. These include polymer extrusion, solution casting and particulate leaching, deposition of a polymer solution stream on a spinning mandrel and manipulation of sheets of polymer meshes. To achieve arbitrary three dimensional geometries, preformed sheets of biomaterial have been cut and laminated with a resolution of 0.8 mm. Such supports are useful for forming the macroscopic shape of the replacement tissue (i.e. an ear for cartilage tissue engineering) or for customizing tissues replacements for individualized patients (i.e. an eye socket for bone tissue engineering).

The properties of the tissue engineered construct emerge from the local response of the cells to their 3-dimensional microenvironment. Therefore it is of great importance to recreate biochemical and structural components of the in vivo cellular microenvironments when designing implantable tissue constructs. This microenvironment can be simulated by patterning of the matrix in which the cells are grown in or on, or by patterning the cells within the matrix. Traditional methods for controlling biomaterial scaffold architecture involve a number of methods, each with its own intrinsic limits related to the materials employed, its resolution or its costs. Injection molding against a microfabricated silicon template was utilized by Kapur et al (1996) with a resolution of 10 microns. A three dimensional printing technique developed by Griffith et al (1998) utilizes a polymer powder spread on a plate. The resolution of this method is dependent upon the polymer particle size where the typical features are on the order of 300 microns. These techniques are useful for forming complex tissues such as bone/cartilage composites for the knee and for optimizing microscale architecture to improve the function of the resultant tissue. For example, scaffold texture can alter cell migration, ingrowth, vascularization, and host integration. Microscale scaffold architecture can also modify the cellular responses such as growth and differentiation as has been shown on three-dimensional polymer meshes (e.g. U.S. Pat. No. 5,443,950).

Methods to prepare scaffolds with microscale structure that are more amenable to use with biodegradable polymers such as poly-DL-lactide-co-glycolide (PLGA) have also been developed. Material microstructure was first controlled by process parameters such as the choice of solvent in phase separation, doping with particulate leachants, gas foaming, woven fibers, and controlled ice crystal formation and subsequent freeze-drying to create pores; however, these scaffolds lack a well-defined organization that is found in most tissues in vivo (i.e. pores are randomly distributed rather than oriented and organized in functional units). Similarly, microtubular scaffolds (Ma and Zhang, 2001); 3-dimensional micropatterned scaffolds using UV polymerization (Ward et al., 2001) produce scaffolds with arbitrary architectures. The use of soft lithography methods using biopolymers such as poly(dimethylsiloxane) (PDMS) allows for the production of high resolution 2-dimensional scaffolds that may be assembled into higher order structures (Vozzi et al., 2003). However, the method is cumbersome for the production of 3-dimensional structures as the maximum thickness possible for each scaffold layer is about 30 microns.

None of the methods discussed above allow for the generation of more, complex cellular tissue constructs in which cells can be placed in specified 3-dimensional configurations throughout a thick construct. For example, biomaterial scaffolds must be seeded with cells with the help of gravity, centrifugal forces or convective flow (Yang, et al., 2001). Alternatively, cells can be recruited to the graft by the use of growth factors and chemokines (Badylak et al., 2001). Many of the techniques described above require processing conditions such as heating and polymer grinding that may be limiting for the inclusion of bioactive moieties and preclude the formation of scaffolds in which the cells are cast in the scaffold. In the methods discussed above, the cells are patterned based on the physical structure of the surfaces of the scaffold. None of these methods enable formation of a thick tissue construct that is populated with living cells.

A number of methods have been developed for the generation of essentially two dimensional cell arrays. Cells may be positioned in or on a substrate using mechanical methods such as pipette/syringe placement (e.g. Landers et al., 2002), stenciling (Folch et al., 2002) and microfluidic delivery (Folch et al., 1999) and by optical methods such as optical tweezers (reviewed by Ashkin, 1991) and laser-guided writing (Odde et al., 2000). Electromagnetic forces such as elelctrophoretic, dielectrophoretic (DEP) (Matsue et al., 1997) and magnetic attraction/repulsion, may also be used for bulk patterning of cells in a two dimensional space. However, in the absence of an appropriately adhesive substrate, the cells return to a random state after the electromagnetic forces are removed. Moreover, patterning of cells in 2 dimensions is of limited utility for long term maintenance of differentiated cells. Cells sitting on a 2-dimensional surface often spread and lose function depending on both the cell types to be cultured and the size of the regions of each cell type. Chondrocytes, for example, have a rounded morphology in vivo and cease normal biosynthetic activity upon spreading into a flattened shape on a 2-dimensional surface. Methods of coculturing have been used with some success to maintain hepatocytes in a differentiated state. However, these methods are cumbersome and are typically not useful for long term maintenance of cells in culture. Bhatia et al. (U.S. Pat. Nos. 6,130,479 and 6,133,030) teach methods of patterning various cell specific adhesion molecules (e.g. collagen) on glass slides using photoresist, a UV-sensitive polymer, and photolithographic techniques. Maintenance of a differentiated, state in hepatocytes was dependent on the ratio of surface to perimeter of the islands of hepatocytes within the non-parenchymal cells. High resolution patterns (10 microns) can be generated for the co-culture of cells with, different adhesion properties, however, the method is still limited to only two dimensional patterns and great care must be taken to maintain the cells in the desired state.

Methods have been developed for patterning of cells within a matrix by patterning molecules within the cell seeded microenvironment, by magnetic orientation of fibrin in gels (Dubey, 2001) or by stretching an underlying support (Vandenburgh et al, 1982). However, these methods orient all cells in a volume in a constant orientation, either linear or radial. Specific microscale patterning and positioning is not possible. Cells may be encapsulated in a 3 dimensional support, such as a hydrogel, but it is not possible to achieve specific cell patterns or orientations. These methods do not allow for the precisely placement of cells in a matrix; rather a population of cells is generally oriented or confined to a specific volume much larger than the cell.

Hydrogels are becoming an increasingly popular material for tissue engineering because their high water content and mechanical properties resemble those of tissues of the body. In addition, many of the hydrogels can be formed in the presence of cells by photopolymerization, which allows homogeneous suspensions of cells throughout the gel. Poly(ethylene glycol) (PEG)-based hydrogels are of particular interest because of their biocompatibility, hydrophilicity and the ability to be customized by changing the chain length or chemically adding biological molecules (Peppas et al., 2000, incorporated herein by reference). These types of hydrogels have been used to homogenously immobilize various cell types including chondrocytes (Elisseeff et al., 2000) vascular smooth muscle cells (Mann et al., 2001) and fibroblasts (Gobin and West, 2002; Hem and Hubbell, 1998) that can attach, grow and produce matrix.

One property of these hydrogel systems that has not yet been exploited is the use of the photopolymerization step to form structural 3-dimensional hydrogel features containing cells. Elsewhere in non-biological systems, the fundamentals of photolithography have indeed been applied to PEG-based hydrogel systems to create hydrogel valves within flow systems by controlling regions of photopolymerization using a mask (Beebe et al., 2000). This process would not be amenable to the incorporation of living cells due to the harsh chemical conditions and the high density polymers with short polymer chains used to obtain high resolution structures.

One goal of tissue engineering is the production of artificial tissues or organs for transplant (e.g. cartilage). Cartilage, for example, is an avascular tissue with, little or no capacity for effective repair following traumatic injury, due to a limited cell population near the injury that is encased in a dense matrix. Surgical transplantation of cartilage tissue improves patient function in the short-term but suffers from limited donor supply and donor site morbidity. Therefore, tissue engineering approaches are in development to address the tissue sourcing problem by forming cartilaginous constructs from minor biopsies. However, producing such constructs with appropriate biological and mechanical properties requires an understanding of the complex cellular architecture and, potentially, a method for controlling the cellular architecture.

Another goal of tissue engineering is to develop organ support systems such as an artificial liver apparatus, similar to a kidney dialysis apparatus, for hepatic support in individuals waiting for liver transplant. A number of artificial liver devices have been developed (e.g. Naughton, U.S. Pat. No. 5,827,729, incorporated herein by reference), most of which require viable, differentiated hepatic cells in order to function. The liver is a more complex organ than the kidney which is predominantly responsible for salt balance and filtering of molecules based on size. The liver is responsible for detoxification of xenobiotics and hormones, energy metabolism, production of plasma proteins, and production of bile, rather than the simple filtering, of the blood. Furthermore, the factors that lead to hepatic coma in patients suffering from liver failure have not been identified. Therefore, sustenance of a patient in liver failure with a device that lacks hepatic cells is unlikely.

The development of a method to allow for the growth and maintenance of primary hepatocytes would be useful in developing a better understanding of drug metabolism and interactions. A simulated liver could be used desirable for the testing of drugs, both alone in the process of drug development, and to better understand drug interactions (Hodgson, 2001). Initial drug testing is typically performed on cells in culture to facilitate high throughput screening. However, compounds ingested by a patient must have desirable ADMET (Absorption, Distribution, Metabolism, Elimination and Toxicity) properties in order to be successful as a drug. Such tests can be performed in animals, however there are a number of drawbacks including expense, variation between species, and growing disfavor of the use of animals in research by the general public. However, the maintenance of a culture of differentiated hepatocytes is non-trivial. Systems to study the effects of liver metabolism include the use of liver slices, immortalized cell lines and isolated liver enzymes have been developed. Each system is limited by various factors including variability between species, phylogenetic drift of cell lines and possible inaccuracies of using liver enzymes in isolation. The development of a method to allow for the growth and maintenance of primary hepatocytes would be useful in developing a better understanding of drug metabolism and interactions.

SUMMARY

In one embodiment, the invention is a series of methods for the formation of patterned 3-dimensional biopoolymer scaffolds containing living cells in patterned arrays. The cells may be patterned by the manipulation of the biopolymer 3-dimensional structure using selective photopolymerization providing a resolution comparable to tissue. Alternatively, cells may be patterned within biopolymer before polymerization providing a relatively homogeneous slab of biopolymer providing a resolution of single cells upon polymerization. Additionally, the methods may be combined, patterning the cells within the biopolymer before polymerization and subsequently using photopolymerization to fix only limited portions of the patterned cell in the biopolymer.

In one embodiment, the invention is a photolithographic method for the formation of structural features in photopolymerizable biomaterials, preferably PEG-based biomaterials, containing living cells. The method comprises the use of photolithography masks that can be used to localize light in a specific micropattern, while simultaneously barring oxygen transport to the hydrogel. The cells that are suspended in the illuminated regions are thus immobilized in the resulting gels and the newly formed three-dimensional constructs are released from the reaction chamber. Various three-dimensional architectures of these cellular constructs can then be produced at the microscale and in large numbers. The method can be used for the patterning of single or multiple cell types as well as for the creation of multilayer structures.

In one embodiment, the invention is a method to create firm 3-dimensional hydrogel slabs or patterned arrays containing precise patterns of living cells embedded therein. The invention comprises the use of dielectrophoresis (DEP) for patterning of cells in biomaterials, preferably PEG-based biomaterials and subsequent polymerization of the biomaterial to fix the cells in place. DEP force is advantageous for cell manipulation and patterning because it is spatially- and temporally-controllable, non-contact, tunable (by electric field properties), relatively non-cytotoxic, rapid (patterning may be established within minutes) and parallel (i.e. all particles move simultaneously). The method can be used for the patterning of cells, organelles, bioactive particles (e.g. liposomes or gel microspheres containing bioactive agents) or macromolecules within the hydrogel. The method allows for the precise localization of living cells with cell-scale resolution, within a firm hydrogel biomaterial, to the extent that a cells physical microenvironment (e.g. cell-cell and cell-matrix interactions) can be controlled in three-dimensions.

In one embodiment, the invention is a mathematical model that predicts patterning efficiency for various biomaterial properties, cell types and patterns using DEP. This mathematical model has been validated with several microsphere experiments and found to be highly predictive for the amount of time and applied voltage/frequency required for the positioning of cells and particles in various patterns within biocompatible gels of different densities, viscosities and sizes. In one embodiment, the invention is an apparatus formed by the methods of the invention comprising a 3-dimensional hydrogel scaffold containing living cells patterned in a defined manner. Cells can be patterned within relatively homogeneous slabs of hydrogel or by patterning the hydrogel itself. The hydrogel and/or cells therein may be patterned in single or multiple layers and may be of one or more types. The resolution of the patterns are from the single cell level (<10 microns) to a few millimeters.

In one embodiment, the invention is the use of 3-dimensional hydrogel structures containing living cells for any of a number of applications including, but not limited to, artificial tissues and organs for implantation (e.g. cartilage, artificial liver) or in an organ support apparatus (e.g. artificial liver); a system for the evaluation of drug activity and interactions; single-cell or multi-cell arrays for high-throughput screening and a bioreactor for production of proteins and/or metabolites.

DETAILED DESCRIPTION

Figure 1:
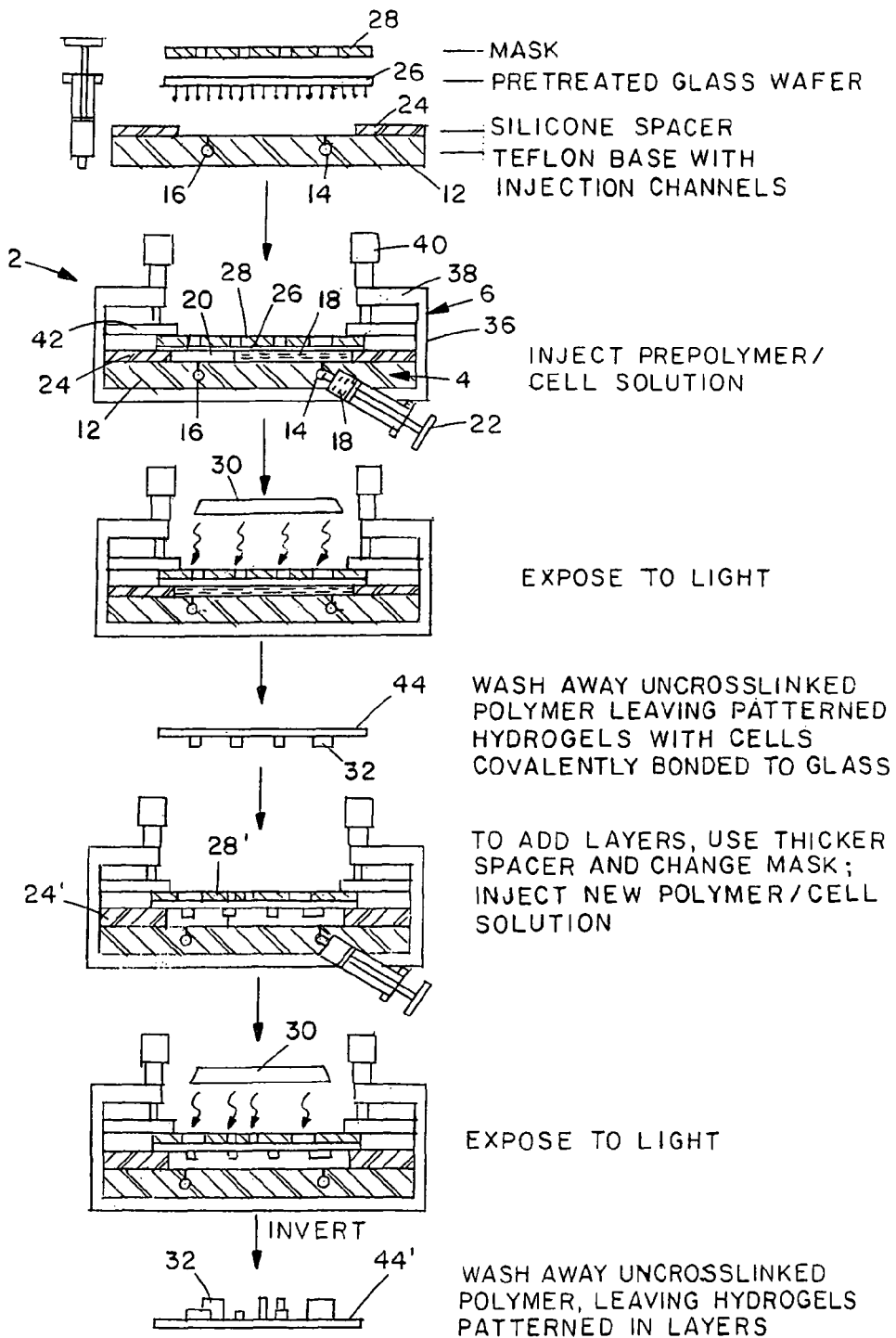
FIG. 1. Process for formation of hydrogel microstructures containing living cells.

The fabrication of 3-dimensional scaffolds that mimic the in vivo cellular microenvironment is of fundamental importance to the success of tissue engineered constructs. Both scaffold chemistry and architecture can influence the fate of function of engrafted cells. While several methods have been developed to control scaffold architecture, each method has intrinsic limits related to resolution, necessary infrastructure or versatility. Although a number of methods have been developed for high resolution 2-dimensional patterning of cells on various supports, no methods are available for the patterning of cells within 3-dimensional scaffolds.

The instant invention provides methods for 3-dimensional patterning of cells within a 3-dimensional scaffold by providing a photopolymerization method for the formation of a hydrogel scaffold with the desired 3-dimensional structure or by patterning the cells within hydrogel scaffold by DEP. DEP can be used alone for patterning of cells in relatively homogeneous slabs of hydrogel or in conjunction with the photopolymerization method. The methods allow for the formation of three dimensional scaffolds from hundreds of microns to tens of centimeters in length and width, and tens of microns to hundreds of microns in height. A resolution of up to 100 microns in the photopolymerization methods and possible single cell resolution (10 micron) in the DEP method is achievable. It is understood that all of the methods of the invention involving the deposition of cells are carried out in a sterile manner. Additionally, the use of hepatocytes and chondrocytes are exemplified herein; however, it is understood that the methods of the invention can be applied to any cell type that is viable in the biopolymer scaffolds described herein.

Biopolymers suitable for use with the instant invention include any polymer that is gellable in situ, i.e. one that does not require chemicals or conditions (e.g. temperature, pH) that are not cytocompatible. This includes both stable and biodegradable biopolymers. The photolithography method requires the use of polymers in which polymerization can be promoted by exposure to an appropriate wavelength of light (i.e. photopolymerizable) or a polymer which is weakened or rendered soluble by light exposure or other stimulus. The DEP method preferably uses a photopolymerizable polymer; however, any polymer with activatable or sufficiently slow polymerization kinetics to allow for patterning of the cells before polymerization can be used in the DEP method of the invention. Polymers that can be used in the methods of the invention include, but are not limited to, PEG hydrogels, alginate, agarose, collagen, hyaluronic acid (HA), peptide-based self-assembling gels, thermo-responsive poly (NIPAAm). Although some of the polymers listed are not innately light sensitive (e.g. collagen, HA), they may be made light sensitive by the addition of acrylate or other photosensitive groups. A number of biopolymers are known to those skilled in the art (Bryant and Anseth, 2001; Mann et al., 2001; and Peppas et al., 2000; all incorporated by reference). As the development of biopolymers is ongoing, it is understood that the exact selection of biopolymer for use is not a limitation of the invention. Any cytocompatible polymer with the appropriate polymerization properties can be used in the invention. The selection of appropriate polymers is well within the ability of those skilled in the art. The biopolymers may additionally contain any of a number of growth factors, adhesion molecules, degradation sites or bioactive agents to enhance cell viability or for any of a number of other reasons. Such molecules are well known to those skilled in the art.

A photoinitiator is a molecule that is capable of promoting polymerization of hydrogels upon exposure to an appropriate wavelength of light as defined by the reactive groups on the molecule. In the context of the invention, photoinitiators are cytocompatible. A number of photoinitiators are known that can be used with different wavelengths of light. For example, 2,2-dimethoxy-2-phenyl-acetophenone, HPK 1-hydroxycyclohexyl-phenyl ketone and Irgacure 2959 (hydroxyl-1-[4-(hydroxyethoxy)phenyl]-2methyl-1propanone) are all activated with UV light (365 nm). Other crosslinking agents activated by wavelengths of light that are cytocompatible (e.g. blue light) can also be used with the method of the invention.

Figure 3:
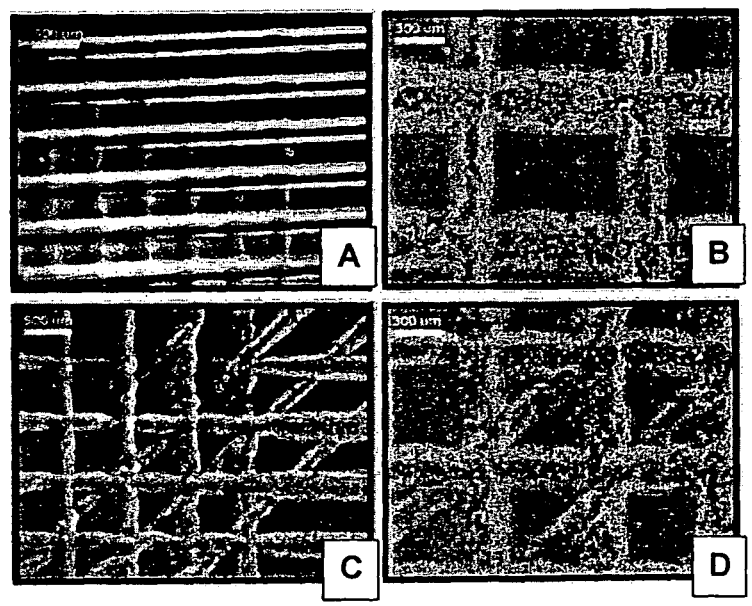
FIG. 3. Examples of single and mutilayer hydrogel microstructures containing living cells. (A) Two layers of patterned PEGDA lines (B) Two layers of patterned PEGDA lines containing cells (C) Three layers of patterned PEGDA lines containing cells at low magnification (D) Three layers of patterned PEGDA lines containing cells at high magnification.

Patterned cells of the invention are localized in specked locations that may occur in repeating structures within 3-dimensional biopolymer rather than being randomly localized throughout 3-dimensional slab of biopolymer, on the surface of a regularly or irregularly shaped 3-dimensional scaffold, or patterned on a 2-dimensional support (e.g. on a glass slide). The cells can be patterned by locating the cells within specific regions of relatively homogeneous slabs of biopolymers (resolution up to about 5 microns) or by creating patterned biopolymer scaffolds of defined patterns wherein the living cells are contained within the hydrogel (resolution up to about 100 microns). Patterning is performed without direct, mechanical manipulation or physical contact and without relying on active cellular processes such as adhesion of the cells. This substantially increases the number of cells that can be efficiently patterned in a short period of time (minutes and increases patterning efficiency (number of patterned cells/total cells)). The cells are patterned by selective polymerization of the biopolymer or by patterning of the cells using an electrical field or both. Theoretically a single cell can be patterned by locating it in a specific position within a biopolymer; however, it is preferred that a plurality of cells, at least 10, preferably at least 20, more preferably at least 100, most preferably at least 500 cells, are patterned. Patterning does not require localization of all cells to a single, discrete location within the biopolymer. Cells can be localized, in lines one or two (see FIG. 7C) or many (FIG. 3B-D) cells wide, or in multiple small clusters (see FIG. 9D) throughout a relatively homogeneous biopolymer scaffold (e.g. approximately 20,000 clusters of 10 cells each in a single scaffold). The 3-dimensional patterning can also include patterning of cells or other particles in a single plane by DEP as the cells are contained in a three dimensional scaffold. This is distinct from patterning of cells on a glass slide as the cells are contacted on all sides by the biopolymer. The cell patterning methods of the invention, can also be used for patterning of organelles, liposomes, beads and other particles.

Relatively homogeneous slab of biopolymer refers to a polymerized biopolymer scaffold that is approximately the same thickness throughout and is essentially the same shape of the casting or DEP chamber in which it was polymerized.

Patterned biopolymer scaffold refers to a biopolymer scaffold that is of a substantially different shape than the casting or DEP chamber in which it was polymerized. The pattern could be in the form of shapes (e.g. circles, stars, triangles) or a mesh or other form. In one embodiment, the biopolymer is patterned to mimic in vivo tissue architecture, such as branching structures. A photopolymerization apparatus is an apparatus such as the one shown in FIG. 1. The apparatus includes a sealable polymerization chamber with at least one transparent surface on which a photopolymerization mask can be placed, and two ports through which fluids and air can be introduced or purged.

Figure 6A:
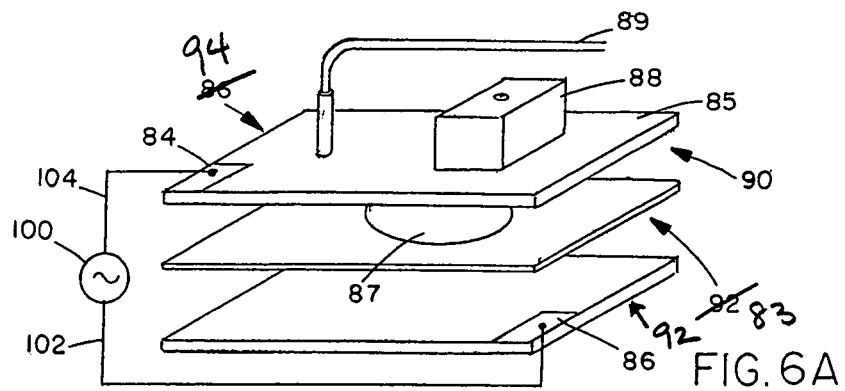
FIG. 6. (A) Schematic of DEP patterning apparatus; and (B) schematic of the DEP patterning method.

A DEP apparatus for the generation of three dimensional biopolymer scaffolds is an apparatus such as the ones shown in FIGS. 6A and B wherein the chamber additionally including a sealable gasket, preferably between the two glass plates/electrodes resulting in an air tight, enclosed chamber. The apparatus further includes two ports through which fluids and, air can be introduced or purged. Alternatively, an open chamber can be used when all of the electrodes are on the bottom of the chamber. The gasket is then sealed to the bottom slide and materials can be exchanged through the opening on the top of the chamber. The electrodes are arranged in the desired pattern and attached appropriately to a power supply to create the desired pattern of cells or other particles.

A method and apparatus have been developed to create biopolymer microstructures containing living cells within a single layer or in multiple patterned layers. The apparatus allows photopolymerization of biopolymers of various heights that can be patterned using masks, preferably emulsion masks (FIG. 1). The apparatus 2 includes a casting chamber 4 and a support apparatus 6 to retain the components of the casting chamber in fixed positions during the photopolymerization process. The casting chamber includes a base 12, preferably made out of Teflon® (poly(tetrafluoroethylene), PTFE) with injection channels 14 and 16. The base provides a surface on which the polymer sits, and prevents adhesion such that the hydrogel can be easily removed after polymerization. The cell-containing hydrogel solution 18 is introduced through one of the two channels into the interior of the casting chamber 20 using a syringe 22 or other injection apparatus (e.g. pipet) and air is released from the chamber through the other injection channel. A single spacer 24 (preferably silicone), of the desired thickness (50-1000 microns) with a single opening of the desired shape is placed on the base 12 and the periphery of the opening forms the wall of the interior of the casting chamber 20. The height of the hydrogel is varied by using silicone spacers of different thickness. Because the photopolymerization free radical reaction is quenched by oxygen, it is necessary to contain the prepolymer solution within a closed chamber while exposing to UV light. The top of the casting chamber is formed with a pretreated glass wafer 26. The glass wafer placed on top of the spacer both allows transmission of UV light from a light source 30 and also acts as a surface to which the hydrogel adheres. It has been found that the hydrogel features 32 lift off the glass wafer when submerged in buffer solution. This problem was solved by pretreating the glass with 3-(trimethoxysilyl) propyl methacrylate, thereby leaving methacrylate groups on the surface that would covalently bind the hydrogel during photopolymerization. Any equivalent crosslinking reagent not toxic to the cells could also be used. The glass wafer is overlaid with a photopolymerization mask 28 with the desired pattern. Masks are generated using graphics software, such as Corel Draw 9.0, and printing using a high resolution printer such as a commercial Linotronic-Hercules 3300 dpi high resolution line printer. Other masks, such as chrome masks, may also be used with the method of the invention.

The components of the casting chamber 4 are assembled within a support apparatus 6. The support apparatus is appropriately sized to hold all of the components of the casting chamber securely during the photopolymerization process. The support apparatus is comprised of a base 34, sidewalls 36 and a partial cover 38 through which screws 40 or other tighteners pass and, contact the retaining plate 42 that contacts the top of the glass wafer 26 on a portion of the glass plate that is directly over the spacers 24. The height of the gel can be controlled by the thickness of a series of rigid spacers. As each thicker layer of the scaffold is added, the complete apparatus is disassembled and the spacer is exchanged for a thicker spacer. Alternatively, the spacers may be made of a compressible material and the screws may contain calipers or micrometers to allow for the thickness of the gel to be increased as layers of the scaffold are added. Rather than completely disassembling the apparatus, the interior of the casting chamber is thoroughly flushed between rounds of photopolymerization.

In the method provided herein, which is described in more detail in the examples and shown in FIG. 1, the photopolymerization apparatus 2 is assembled with spacers 24 of the appropriate thickness and a mask 28 to produce the desired pattern of hydrogel 32 for the first layer. The cells are mixed with the hydrogel prepolymer and the photoinitiator which is added to the mixture just before injection. The mixture 18 is injected into the interior of the casting chamber 20 through one of the injection channels 14, and the air in the chamber is vented through the other injection channel 16. The prepolymer containing cells is exposed to light, of an appropriate wavelength for a defined time period. In one embodiment, the prepolymer containing cells are exposed to light through the mask. In another embodiment, other ways of photopatterning are used including, but not limited to, shining light through an emulsion mask, and also including shining light in a pattern through a digital pattern generator or scanning a laser in a pattern as in stereolithography or using a hologram. The latter embodiments broaden the adaptability of the methods provided herein, increase speed of fabrication, automate fabrication and give the potential to map human clinical scan data to a custom-made tissue engineered replacement. Such methods may also increase resolution. Details are provided for the use of PEG-based hydrogels; however, any photopolymerizable biomaterial with the appropriate, kinetics and low cytbtoxicity can be used. After polymerization, the casting chamber is either flushed with an isotonic saline solution (e.g. phosphate buffered-saline) to remove the unpolymerized biopolymer and cells, or it is disassembled. If additional patterned hydrogel of the same thickness as the first layer is desired, the chamber is flushed, the mask is not changed, additional cells in the biopolymer are injected info the casting chamber and polymerization is performed. If thicker patterned layers are to be added, the chamber is cleaned and reassembled with thicker spacers 24'. Alternatively, if compressible spacers are used, the screws can be loosened to increase the amount of space between the casting chamber base and the glass wafer, the casting chamber can be flushed, and the screws can be readjusted for the desired height of the next layer. A new mask 28' is placed over the glass wafer to provide a different pattern of hydrogel. Again, the cells, prepolymer and crosslinker are mixed and injected into the interior of the injection chamber. The prepolymer is exposed to UV light to photopolymerize the biopolymer. The chamber is then either disassembled or flushed. The scaffold may be used, or an additional layer may be added. The possible number of layers that may be added is dependent on the total thickness of the scaffold, as light scatter increases with the thickness of the gel resulting in decreased pattern resolution during photopolymerization. The photopolymerization method of the invention allows for the formation of scaffolds up to a few (=3 mm thick) when larger feature sizes are desirable.

The method can be used for the production of any of a number of patterns in single or multiple layers including geometric shapes (FIGS. 2A and B) where the cells are patterned into different geometric shapes (A) or a repeating series of dots (B) with the features in various sizes. Alternatively, multilayer biopolymer gels can be generated using a single mask turned in various orientations (FIG. 3A-D, Example 7). In the scaffolds shown in FIG. 3, each layer contains a different cell type; however, a single cell type can be used in all layers. Similarly, a mixture of cell types can be deposited in a single layer. The inclusion of cells in all layers of a scaffold is not required. Cell-containing and non-cell-containing layers can be fabricated adjacent to each other. Non-cell-containing layers may contain bioactive compounds or other factors that can be designed to release active agents at various rates allowing for the generation of gradients or sustained time release of agents.

In the method of the invention, pattern fidelity is fairly high for features on the order of hundreds of microns, whereas feature magnification was observed for smaller feature sizes. This may be a limitation for creating very small features on the order of a few cells, but the achievable resolution is sufficient for producing complex 3-dimensional structures that vary on the same length scale of most tissues (~100 microns), (Bhatia and Chen, 1999). Resolution was found to be dependent on UV exposure, with lower exposure resulting in higher pattern resolution. Initiator concentration did not affect the resolution of hydrogel patterning. Thus, the lowest possible initiator concentration should be used that can still initiate crosslinking in order to minimize toxic effects to the cells. The absolute width increase of the lines was not uniform for-all feature sizes. The precise mechanism for increased feature widening at small dimensions is not clear. Hydrogel swelling likely plays a role as the surface area/volume ratio is higher for smaller features. However, since images were taken immediately after photopolymerization in hopes of minimizing swelling effects, there may be a true non-linearity in the process.

Using the photopolymerization system disclosed herein, hydrogel features were generated with greater than 200 micron resolution within 10%, while very small feature sizes (30-50 micron) resulted in feature magnification of up to 200%. Previous methods of patterning hydrogels with higher resolution (<5 micron) have patterned a very thin dehydrated polymer and subsequently hydrated the structure to form a swollen hydrogel (Chen et al., 1998; Yu et al., 2000). This approach is not appropriate for fabrication of hydrogel microstructures containing living cells as they could not survive the drying process. Others have used very small polymer chains and high polymer densities or very high UV intensities (Ward et al., 2001; Beebe et al., 2000) that are also not amenable to cell survival. Because of the use longer polymer chains in the methods and apparatuses disclosed herein, the hydrogel absorbs a larger quantity of water, which is preferable for living cells, but results in large amounts of swelling that can distort the intended patterns.

Figure 4:
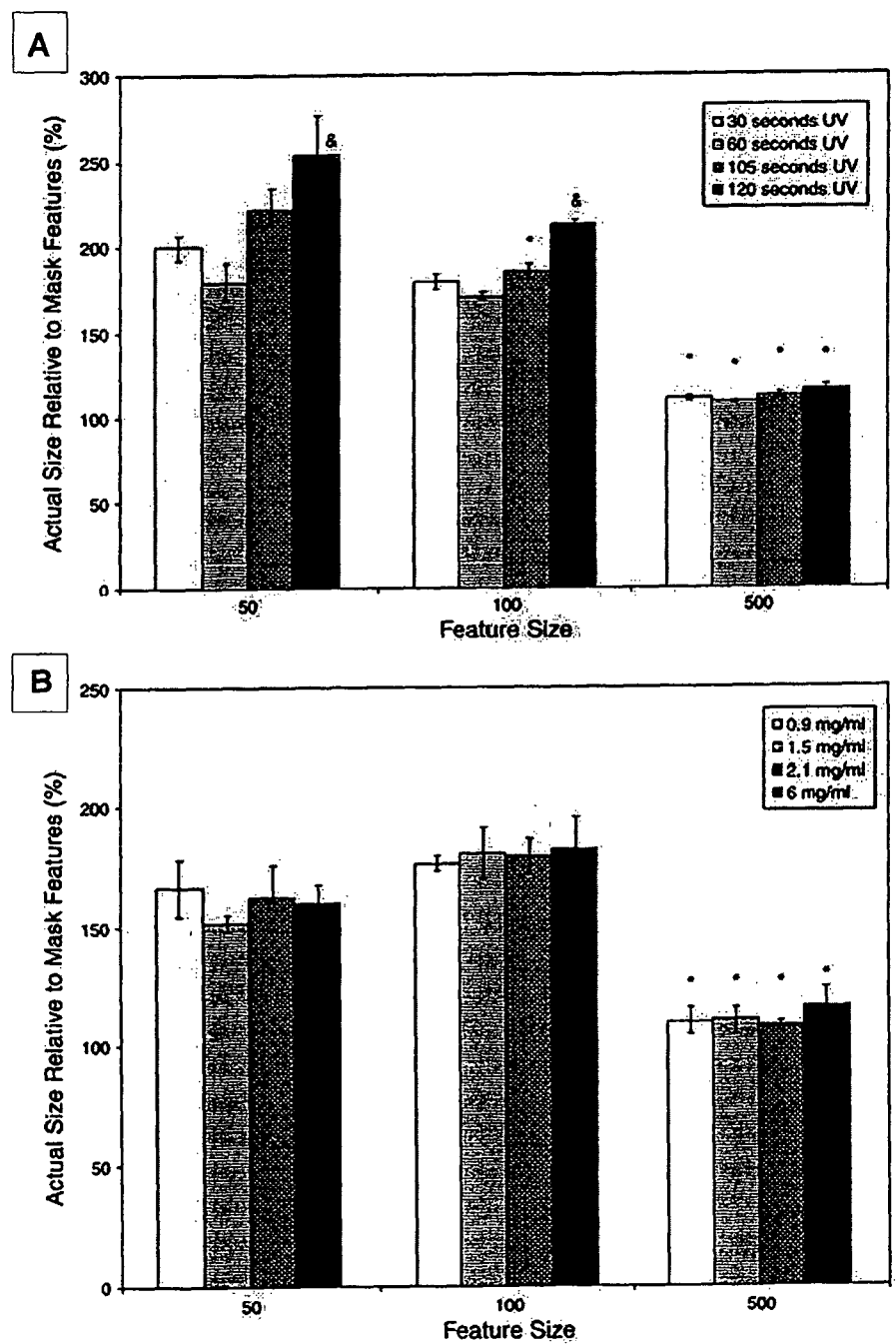
FIG. 4. Resolution and photopatterning. (A) Feature fidelity as a function of feature size and UV exposure. &=p value<0.05 compared to all other UV exposures for the same feature size. *=p value<0.001 compared to all other feature sizes for the same UV exposure time. (B) Feature fidelity as a function of feature size and photoinitiator concentration. *=p value<0.05 as compared to all other feature sizes of the same photoinitiator concentration. The data indicate that UV exposure has an effect on patterning resolution for smaller feature sizes, while photoinitiator concentration does not affect resolution. In addition, patterning of large feature sizes (>200 microns) results in better fidelity regardless of UV or photoinitiator amounts.

There are several parameters that can affect the resolution in the photopolymerization method. The resolution limitations, may be caused by the thickness of the polymer solution layer, the quality of, the emulsion mask, the non-parallel light source, the scattering of light throughout the polymer solution, and the diffusion of radicals throughout the solution. In some configurations, especially larger feature sizes, interesting edge effects were observed (FIGS. 4A-B). This may have been caused by non-uniform transmission of light through the mask or by beam divergence. A more uniform light source and/or focused or collimated light would likely improve the accuracy of the hydrogel photopatterning.

Resolution can also be affected by quenching of the radicals by oxygen. While the polymerization steps were conducted in a sealed chamber, oxygen can be further removed from the system to increase the pattern resolution by bubbling nitrogen gas through the prepolymer solution (Ward et al., 2001) prior to addition of the cells.

In addition to the light source and dosage, other aspects of the biopolymer photopatterning method disclosed herein can also degrade the resolution of the patterns. The use of an emulsion mask may contribute to some loss of feature fidelity. This may be improved upon by use of a conventional chrome mask; however, for the range of feature sizes reported here, the emulsion masks should be sufficient. Emulsion masks offer the advantage of rapid production time and minimal cost.

The thickness of the biopolymer can also impact the feature fidelity. While the 100 micron thickness used is thin as compared to other polymer scaffolds (on the order of millimeters), it is thick as compared to other photopatterned polymers and photoresists, which are typically in the range of 1-25 microns. As the thickness increases, the amount of light scattering also increases, which can significantly affect photopatterning resolution. This parameter can be readily modified by changing the thickness of the spacers and is well within the ability of those skilled in the art. Light scattering is particularly prevalent in the photopatterning system as compared with other photolithographic techniques because of the presence of cells within the biopolymer. A majority, of the feature widening is likely due to the uncollimated light and the swelling of the hydrogel used in the experiments with water after photocrosslinking. Other factors such as the type of initiator, incorporation, of polymerization accelerators, polymer concentration, and polymer chain length may be factors. These parameters can be readily modified and optimized using methods and materials well known to those skilled in the art.

The formation of high resolution patterned cells in 3-dimensions can be achieved by methods other than photopolymerization, such that the limitations of the method are overcome.

Figure 5:
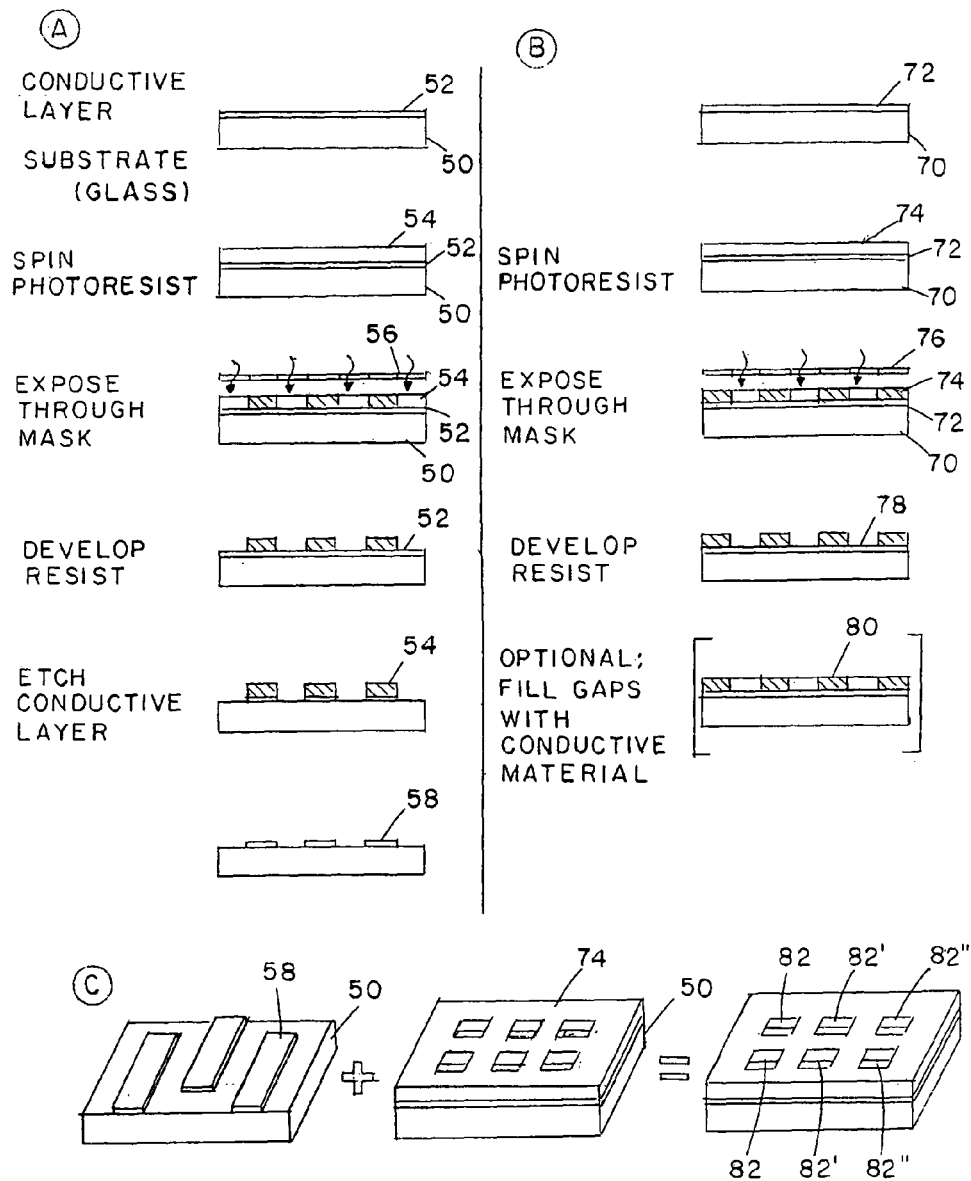
FIG. 5. Electrode array fabrication methods (A) Etch conductive layer; (B) overlay dielectric layer; and (C) combine layers for the generation of more complex electrode arrays.

In DEP, the cell-pattern is determined by the pattern and shape of the electrodes. Electrodes can-be-fabricated to be as small as hundreds of nanometers to as large as the entire patterning chamber (up to centimeters across). In the instant invention useful electrodes are typically no smaller than 3 microns which are used for the patterning of single cells; however, smaller electrodes may, be useful for the patterning of microspheres, liposomes or other particles and their use is within the scope of the invention. Methods of fabrication of patterned electrode arrays are well known to those skilled in the art. Three methods of electrode fabrication are outlined in FIG. 5 for the generation of discontinuous and continuous electrodes; however the method of the invention is not limited by the method of fabrication of the electrode arrays.

Briefly, for the fabrication of independent electrodes for DEP (FIG. 5A), a substrate 50 (e.g. glass) is coated on one side sequentially with a conductive layer 52 (e.g. indium tin oxide (ITO), gold, copper) and photoresist 54. ITO is preferred for use as a conductive layer as it is clear allowing for the visualization of the patterning and polymerization processes and does not inhibit photocrosslinking. The photoresist is then exposed through a mask 56 for an appropriate time depending on the light source and the thickness of the photoresist. Emulsion masks can be used for electrodes down to 15 microns with chrome masks being preferred for smaller electrodes. The photoresist is developed exposing the conductive layer 52. The exposed conductive layer is then etched to remove the conductive material in the areas not covered by the photoresist. The photoresist is then removed to reveal the electrodes 58.

The second method (FIG. 5B), allows for the production of electrically continuous electrodes for DEP. In the method, a glass slide 50 is again sequentially coated with a conductive layer 52 and photoresist 54; exposed to UV light through a mask 56; and the resist is developed. In lieu of etching the conductive layer, the gaps in the photoresist are optionally filled in with a conductive material 60 such as electroplate metal or fill polymer. The two methods can also be combined (FIG. 5C), by using an etched conductive layer 58 in place of a homogeneous conductive layer 72 in the second method.

Such a method can be used to generate multiple independent, continuous electrodes (82, 82', 82").

A method and apparatus have been developed for high resolution, cell-scale patterning of cells in hydrogel using DEP (FIG. 6). The apparatus 90 of the instant invention comprises, preferably, a transparent, closed chamber formed by a bottom 92 and top 94 flat, typically glass, plates. The electrodes shown in FIG. 6A are ITO coated slides with conductive tape, 84 and 86, to serve as attachment points for wires 102 and 104 that are connected to a power supply 100. A number of more complex electrode arrangements are possible. A rubber gasket 83 with an opening 87 inserted between the plates usually defines the dimensions of the chamber. A round opening is shown by way of example. The opening may be of essentially any shape. The chamber further includes fluidic ports for the introduction 88 and purging 89 of the solutions and cell suspensions used in the method of the invention. Alternatively, the chamber may be open when all of the electrodes are on the bottom of the chamber with the thickness of the gel being determined by the amount of biopolymer loaded in the apparatus. The DEP chamber establishes a spatially non-uniform electric field within a rectangular volume, typically 25-500 microns thick, with micropatterned electrodes on the top and/or bottom surface, with features typically 5-100 microns wide, spaced 10-250 microns apart.

The size of the DEP patterning chamber can vary widely depending on the material to be patterned (e.g. cells, beads, liposomes) and the final pattern to be achieved. The biopolymer in which the material is to be patterned must be at least as deep as the diameter of the particle to allow the particle to move, typically about 10 to 25 microns for cells. However, a deeper chamber would be desirable for the patterning of cells to reduce the shear forces on the cells. The maximum depth is also largely dependent on particle size, but also on the type of patterning to be performed. For example, patterning, of, cells using both + and −DEP in a 1 mm deep chamber would be prohibitively, slow and cause damage to the cells. However, patterning of 100 micron diameter particles in a 1 mm deep chamber would not be prohibitively slow. Additionally, if cells were to be patterned exclusively by +DEP which occurs in the plane on top of the electrodes, the depth of the chamber has less of an effect as the particles fall by gravity to the bottom of the chamber, as long as the particles are denser than the patterning media. Such considerations would be well understood by those skilled in the art.

Electrode width and spacing in DEP is determined by the fabrication process, which presently allows for the fabrication of 0.1 micron (100 nm) electrodes. Although such small electrodes cap be used for the patterning of particles using the method of the invention, this is substantially smaller than the diameter of a cell; however, such an electrode can be used for the patterning of organelles or liposomes. In preferred embodiments, electrodes are approximately the size of the cell or particle to be patterned, with a range, of about 10-times smaller to 10-times larger than the particle to be patterned being a reasonable size. This does not prevent having on electrode that is the size of the entire patterning chamber as shown in a number of figures. Electrode spacing is limited by time scales for patterning. The maximum practical distance for electrode spacing when patterning cells is about 250 microns for cells; however, electrode spacing can be substantially larger (up to about 1 mm) for patterning of non-viable particles with long patterning times.

Figure 6B:
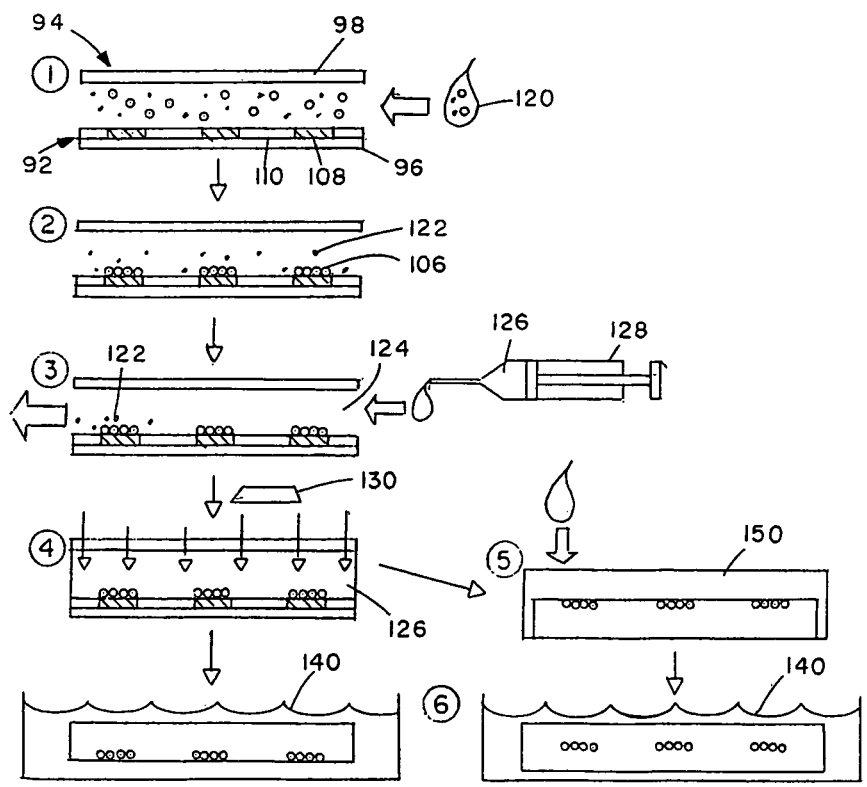
Figure 8:
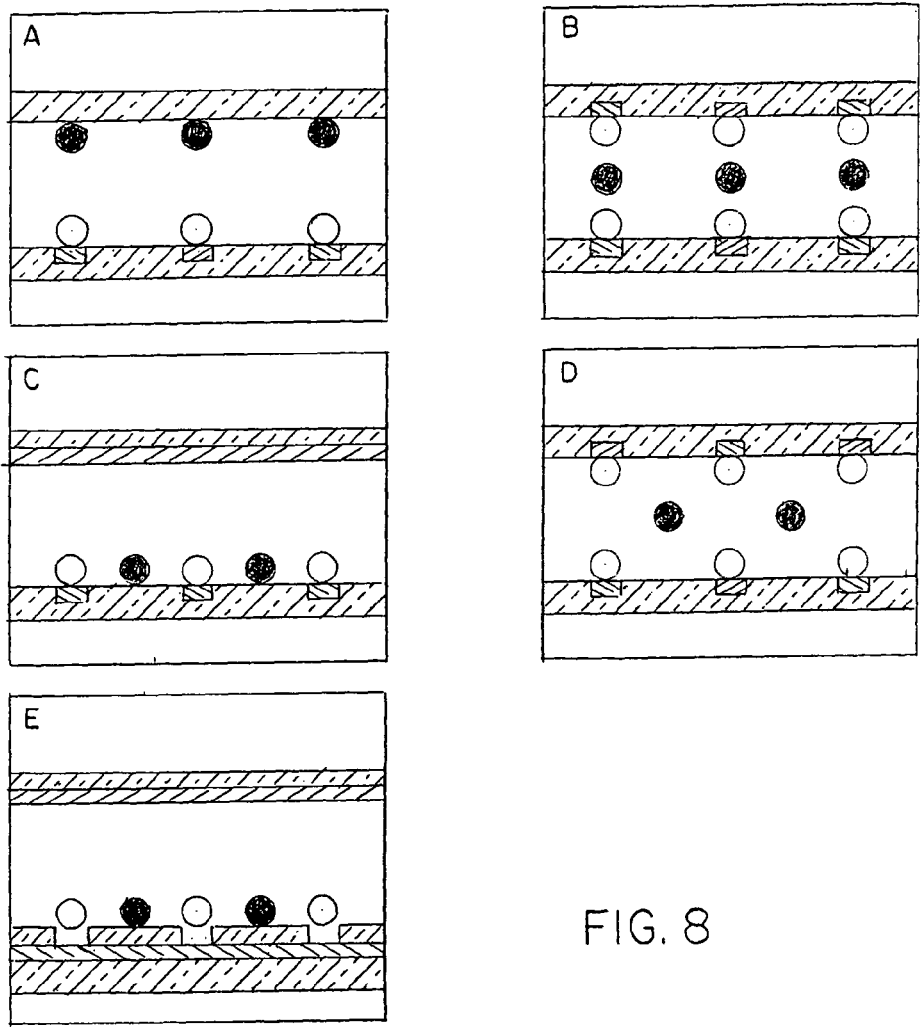
FIG. 8A-E. Schematics of electrode configurations with the positive and negative DEP pattern locations indicated.

A number of DEP apparatuses are known to those skilled in the art (Pethig and Markx, 1997; and Heida et al., 2001, both incorporated by reference). The patterning chamber of the instant invention establishes a highly non-uniform electric field within a rectangular volume typically 100 microns thick. The bottom of the chamber is a glass slide with micropatterned electrodes, typically 5-100 microns wide and spaced 10-250 microns apart, center to center. A simplified schematic of the DEP patterning chamber is shown in FIG. 6B. The chamber 90 shown contains one bottom electrode 92 and top electrode 94, each ITO electrode is supported on a glass slide 96 and 98. In the apparatus shown, the bottom electrode 92 is a discontinuous positive patterned electrode array and the top electrode is a continuous negative 94 electrode; however, other arrangements of electrode types are possible (see FIG. 8). Each electrode or electrode array of the same charge is individually connected to an appropriate power source by separate conductive wires. As shown, the cells 106 pattern on top of the conductive regions 108 rather than the photoresist regions 110 of the bottom electrode.

The method of the invention for fixing the cells in a 3-dimensional support after DEP patterning is shown in a, simplified schematic in FIG. 6B. The electrodes are formed by methods such-as those described in FIG. 5 and the DEP chamber is assembled as shown in FIG. 6A with top 94 and bottom 92 electrodes having the desired pattern. The chamber surface is treated with a blocking agent (e.g. bovine serum albumin (BSA), pluronic, fluorination) to prevent adhesion of cells, particles or the scaffold to the surface. Cells, particles and/or other matter to be patterned suspended in an appropriate buffer 120 are placed in the DEP chamber (1). The patterning buffer is selected based on the types of particles and/or cells to be patterned or separated. A number of appropriate buffers are well known to those skilled in the art. For cell patterning, the buffers must be isotonic and of a physiological pH.

The electric field is turned on for a time and voltage determined by the particles to be patterned and the geometry of the space in which they are to be patterned. For example, patterning an array of particles 100-200 microns apart in hydrogel requires 1-10 minutes at 2-7 volts rms (root mean square) at 15 mHz. Living cells 106 and other particles are patterned according to the electric fields generated by the electrodes. Dead cells 122, which have altered dielectrophoretic properties, remain in suspension and are washed away after DEP with the media in which the cells were patterned (2). The chamber is flushed to remove non-patterned particles. The interior of the DEP chamber 124 is then filled with a photopolymerizable biopolymer 126, preferably a PEG based biopolymer, using a syringe 128 or other transfer device (3) and subjected to an appropriate wavelength of light from a lightsource 130 (4). The hydrogel may be polymerized homogeneously or through a mask to result in selective photopolymerization and patterning of the biopolymer. In another embodiment, other ways of photopatterning are used including, but not limited to, shining light through an emulsion mask, and also including shining light in a pattern through a digital pattern generator or scanning a laser in a pattern as in stereolithography or using a hologram. The polymer is then released from the DEP chamber. The polymerized hydrogel containing cells can be transferred directly into a culture dish containing growth media 140 (6). Alternatively, the slab may be transferred into a chamber for modification by the addition of one or more hydrogel layers 150 (5), with or without patterning, before transfer into a culture dish containing growth media 140.

Figure 7:
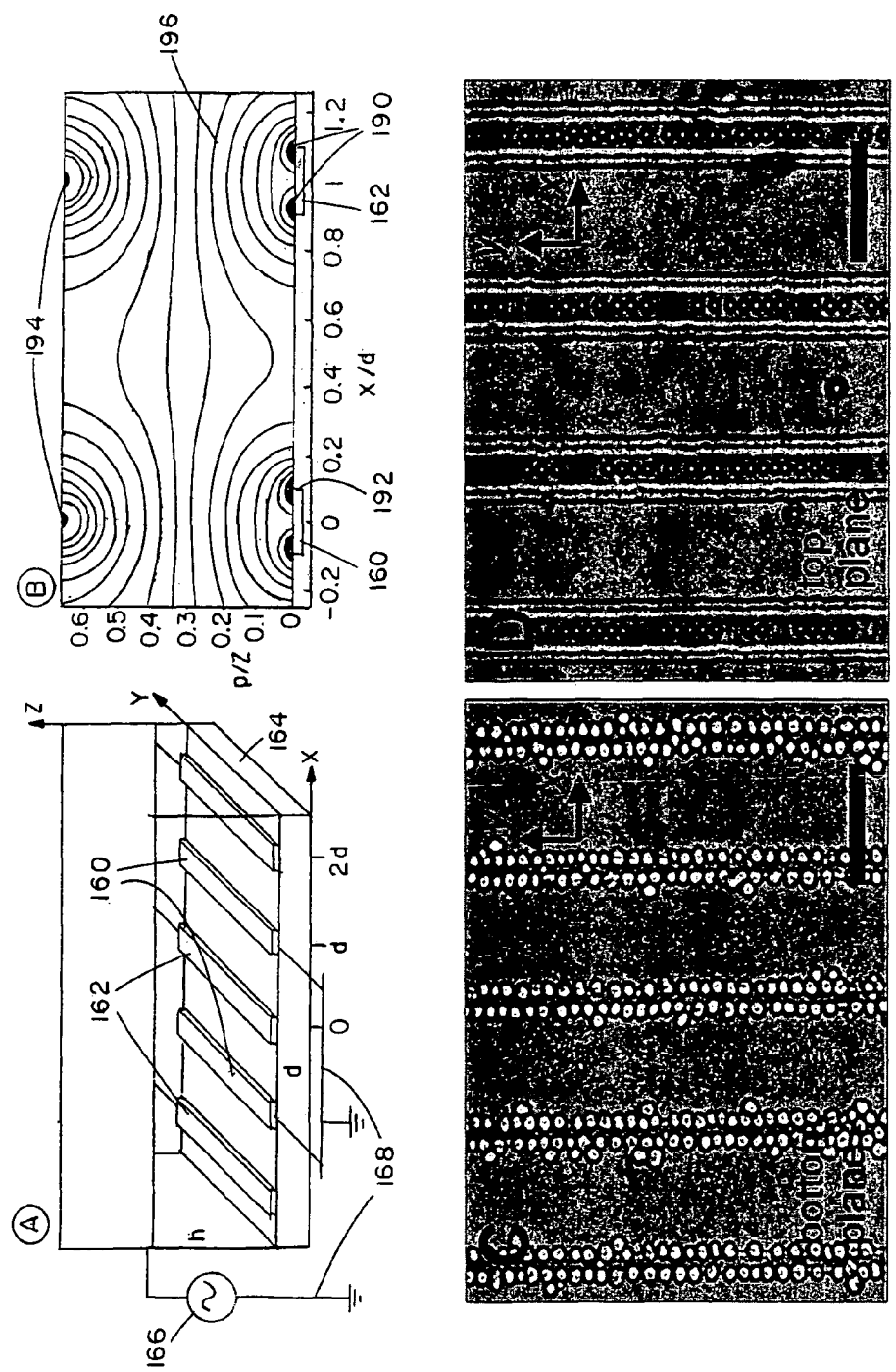
FIG. 7A-D. (A) Schematic of a DEP patterning chamber; (B) the resulting + and −DEP field magnitudes in cross section; and micrographs of (C) +DEP patterned cells; and (D) −DEP patterned beads.

An electrode array electric field magnitude diagram and the resulting patterns from + and −DEP with such an electric field pattern are shown for the electrode pattern shown in FIG. 7. x, y and z axes have been indicated in all portions of the figure to facilitate orientation of the drawings. The electrode array has elongated alternating positive 160 and negative 162 electrodes attached to a glass slide 164. Each electrode is attached to the power source 166 by wires 168. The electric field magnitude diagram shows the highest electrode strength 190 at the electrode edges 192 with each successive line 196 indicating a decrease in DEP field strength and the lowest directly above the electrodes 194. The effects of the field on patterning are shown in FIGS. 7C and D. FIG. 7C is a micrograph showing the patterning of (C) cells at +DEP locations (features ~110 microns apart), the patterning of (D) beads at −DEP locations. The patterning locations can be seen to readily correspond to regions of high and low DEP electric field magnitude resulting in rows of cells two cells wide corresponding to the edges of the electrodes and rows of beads one bead wide corresponding to the space between the electrodes.

For clarity and simplicity, DEP with only a single patterned electrode has been shown initially in the figures demonstrating the method of the invention. However, a number of electrode arrangements are possible allowing for more complex patterning of cells such as those shown in FIG. 8. In each figure, insulating layers (e.g. glass, photoresist), the positive electrodes, the negative electrodes, the −DEP patterned particles and the +DEP patterned particles are shown as indicated. The figures are shown as cross sections wherein the electrodes may be relatively punctuate (e.g. squares, circles) or lines that run the length of the DEP chamber. The DEP patterned objects are localized relative to the electrodes as shown forming either discrete shapes or lines depending on the shape of the discontinuous electrode(s). Electrodes can be generated to allow for patterning of small groups of cells to single cells. This allows for the study of cell-cell interactions on as low, as the single cell-level, up to clusters of tens or hundreds of cells without direct mechanical manipulation of the cells. No prior methods have allowed for the efficient arrangement of large numbers of cells into multiple, reproducible small defined arrays. The schematics shown provide examples of possible arrangements of electrodes. They do not exemplify all of the possible arrangements which could be readily devised by one skilled in the art.

FIG. 8A shows a patterning chamber in which alternating, independent positive and negative electrodes are on the bottom of the chamber with no electrode on the top of the chamber. This results in DEP patterning that is similar to that shown in FIG. 7. FIG. 8B has an electrode array with alternating, independent positive and negative electrodes, with the positive and negative electrodes aligned with electrodes of the same charge across the chamber. This results in patterning of cells on both the top and the bottom of the chamber with −DEP patterning objects (e.g. polystyrene beads) in the center of the chamber. FIG. 8C has a continuous negative electrode on the top and multiple independent positive electrodes on the bottom resulting in alternating areas of +DEP on top of the positive electrodes and −DEP patterning between the negative electrodes in a single plane. FIG. 8D has a pattern similar to FIG. 8B except, electrodes are opposite from electrodes of the opposite charge across the chamber. This results in +DEP patterning both along the top and bottom walls of the chamber adjacent to the electrodes and −DEP patterning on the center of the chamber between the electrodes. Finally, FIG. 8E has a continuous, patterned positive electrode on the bottom of the chamber and a continuous negative electrode on the top of the chamber. This results in a pattern of alternating + and −DEP areas in a single plane along the bottom of the chamber.

Figure 9:
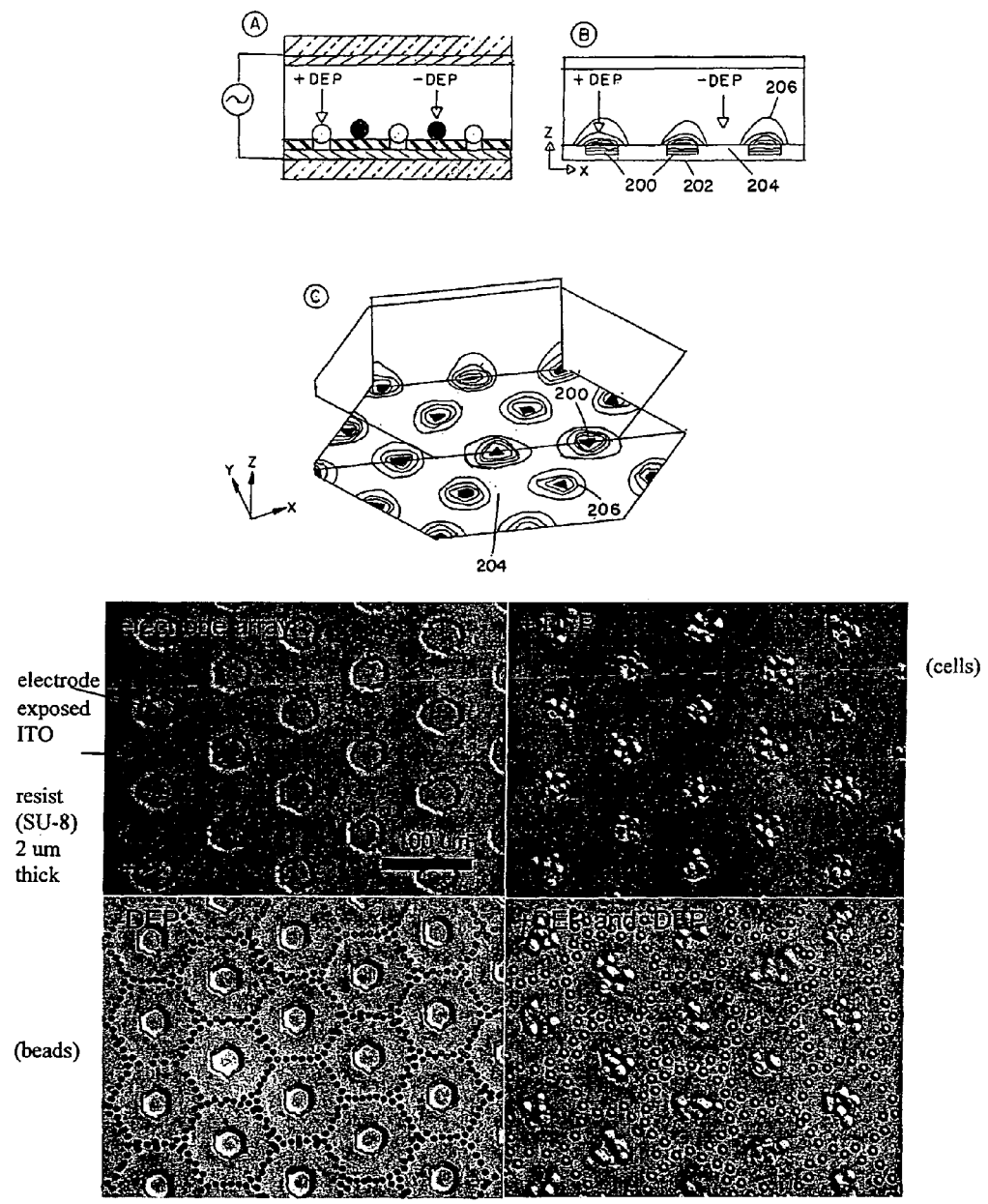
FIG. 9A-D. (A) Schematic of a cross-section of an electrode array and a corresponding field strength diagram in (B) cross-section and in (C) three dimensions; and (D) micrographs of the electrodes, +DEP patterned cells, −DEP patterned beads, and cells and beads patterned simultaneously.

FIG. 9 demonstrates patterning using one of these more complex arrays similar to FIG. 8E, a continuous, patterned positive rounded electrodes on the bottom of the chamber and a continuous negative electrode on the top of the chamber. DEP field strengths are shown in both 2 (FIG. 9B) and 3 (FIG. 9C) dimensions with the regions of highest field strength 200 at the electrodes 202, with the field strength decreasing with each line 206 from the center to the lowest field strength between the electrodes 204.

Patterning efficiency was characterized by the time required for cells within the chamber to move to their patterned locations. DEP force (F), estimated as the first order dipole contribution previously reported (Pohl, 1978), is dependent on particle and fluid properties and the electric field (E):

$$F_{DEP}=2\pi R^3 \in_m Re[f_{CM}(\omega, \in_m^*, \in_p^*)]\nabla |E^2|$$

where R is particle radius, $\in_m$ and $\in_p$ are medium and particle permittivity, respectively, and is the Clausius-Mossotti factor dependent on fluid and particle complex permittivities.

Spatial nonuniformity of the electric field, was calculated by solving Laplace's Equation for electric potential throughout the chamber volume, assuming ideal conductive electrodes and perfectly insulating boundary walls. DEP force was nondimensionalized according to the interdigitated electrode, spacing (i.e. center-to-center distance, d). Model calculations performed in Mathematica (Wolfram Research) were verified using a 3 dimensional finite element model (CFDRC).

During particle motion, DEP force is counteracted by drag force (particle inertia was determined to be negligible). Stokes drag was assumed (Re<$10^{-5}$), except for particles moving along a boundary where Oseen's modification was used. This force balance yielded particle velocity at any point within the chamber, and integration along the particle path resulted in the desired patterning time value. Patterning time (t) is dependent on particle and fluid material properties, and chamber/electrode geometry:

$$t=12\mu d^4/(\in_m V_{rms}^2 f_{CM} R^2)\tau(x, z) \quad (2)$$

where μ is fluid viscosity, d is electrode spacing, $V_{rms}$ is applied potential, and τ is a nondimensional scaling factor dependent on chamber geometry and particle position.

From (2), patterning time increases linearly with fluid viscosity; for example, localization in 3 seconds in water would take 5 minutes in a hydrogel solution with 100-fold higher viscosity. Time t decreases nonlinearly with smaller feature size ($d^4$), larger particle size ($R^{-2}$), and higher applied voltage ($Vrms^{-2}$).

The time scale factor, r, depends greatly on initial particle position and chamber geometry, especially height h. The most efficient patterning, i.e. lowest t, occurs for chamber height between 0.15 and 0.4 times electrode spacing (grey bar), with exponentially increasing patterning time outside this range.

For model validation, a chamber was chosen with 50 micron height and 50 micron wide electrodes spaced 150 microns apart. This corresponds to h/d=⅓, and τ=0.075. Using (2) and material properties for water and polystyrene, the predicted patterning time for a 10 micron particle at x=60 microns from the electrode center is 3.7 seconds. The predicted curve matches experimental data well (n=7 beads).

The model reveals that particle patterning is most efficient with: liquid states of low viscosity, low conductivity, and high permittivity; patterns with small feature size; relatively thin gel thickness; and strong electric fields. However, patterning efficiency is constrained by biological criteria for cell viability, such as appropriate osmolarity and buffered pH, lack of cytotoxic reagents, and limited electric field strength. Therefore, the model is likely to be especially useful for optimizing numerous patterning conditions.

The ability to pattern individual cells provides a method for understanding cell-cell interactions in both 2- and 3-dimensions in tissues. Articular cartilage, for example, has distinct zonal layers: at the articular surface, disk-shaped chondrocytes produce a parallel collagen network and secrete lubricating molecules, whereas deep zone cells are organized into multicellular columnar lacunae surrounded by collagen fibers oriented perpendicular to the surface to resist compressive loads. Understanding the effect of cell shape and cell contact on matrix content and structure (and vice versa) is important for improving tissue-engineered constructs and elucidating the causes and development of osteoarthritis, a progressive and irreversible tissue degeneration. Chondrocytes for use in the instant invention for the study of cells within patterned scaffolds and the use of scaffolds for tissue replacement include primary cells from human, pig or other animal source, immortalized primary cell lines, chondrocyte cell lines, adult stem cell derived chondrocytes (i.e. from oval cells, bone marrow cells) embryonic stem cells and fetal chondrocytes. Furthermore, chondrocytes require a rounded morphology for differentiated function and are therefore not amenable to current 2-dimensional patterning methods. Recent literature suggests that cell seeding density in random 3-dimensional gel culture influences chondrocyte proliferation, gene expression patterns, and quantity and types of matrix molecule secretion, in a complex manner. In these reports, varying cell density affects several factors: nutrient exchange, cell-cell vs. cell-matrix contact, and cell proximity via paracrine signals. To isolate specific microenvironmental effects, chondrocytes can be positioned into 3-dimensional patterns designed to independently specify cell-cell contacts, cell proximity and/or cell shape, while providing constant nutrient exchange, total cell number, and average seeding density. For example, cell clusters of various sizes can be generated to isolate effects cell-cell contact or paracrine signaling, increasing with cluster size. Separating these effects is achieved by patterning cells with an attached pericellular matrix (few microns thick) to prevent physical contacts. Functional assays for matrix production (immunohistochemistry for sulfated GAG and Collagen II), zone-specific proteins (SZP for superficial layer, CILP for mid zone), and proliferation will determine cellular responses for various chondrocyte sources, including mesenchymal stem cells that may differentiate into zonal phenotypes.

Tissues with cell-derived anisotropic properties can be made using the DEP method disclosed herein. These patterned cells in scaffolds are useful for engineering tissues such as cartilage, tendon, and muscle. Chondrocytes, fibroblasts, or myocytes in patterned lines should exhibit anisotropic mechanical properties due to cell orientation and local deposition of matrix molecules. These effects are assayed by measuring mechanical stiffness in orthogonal directions. Additionally, physical properties of the deposited extracellular matrix (ECM), such as extent of collagen fiber crosslinking and fiber orientation, can be studied with chemical assays and polarizing microscopy. Understanding ECM formation in this controlled in vitro environment will help to improve integration of engineered constructs with native tissues, which requires a physical matrix linkage across the interface and remains a significant challenge for current tissue engineers.

The method of DEP patterning can be combined with methods for patterning of hydrogel. A combined method could be exceptionally useful for the culture a first type of cell that are intimately associated with a second type of cell in vivo making their isolation by mechanical means difficult. The mixed cell population can be patterned to isolate the two cell types, and selective photopolymerization can allow for the binding of one cell type into the matrix without the other. The combination of methods can also be useful for creating cell-laden constructs where cells are patterned on multiple length scales (e.g. less than 10 microns by DEP patterning and hundreds of microns via photopatterning). This would allow for constructs with defined 3-dimensional bulk shape and defined 3-dimensional cellular position within. Also, the combination of methods can be useful for the patterning of cells that are difficult to isolate from cells with which they grow in vivo or on particulate supports on which they grow in vitro by segregating the two populations using DEP and subsequently fixing only one type into the biopolymer using photopatterning. Alternatively, by photopolymerizing only the areas of +DEP, predominantly living cells are incorporated into the matrix.

Example 1

Hydrogel Chemistry

PEGDA hydrogel chemistry was based on a protocol previously described by West and co-workers (Mann et al., 2001). Poly(ethylene glycol)diacrylate (PEGDA) (3.4 kDa; Shearwater Polymers, Huntsville, Ala.) was dissolved in HEPES buffered saline (pH 7.4) to form a 20% w/v solution. The photoinitiator 2,2-dimethoxy-2-phenyl-acetophenone (Sigma, St. Louis, Mo.) dissolved in 1-vinyl-2-pyrrolidinone (300 mg/mL) (Sigma) was added to the prepolymer solution immediately prior to UV exposure. The solution was then exposed to a UV light source (VWR, cat. no. 36595-020) at 365 nm and 10 mW/cm2 to crosslink the polymer and form the hydrogel. The photocrosslinking reaction involves the formation of a reactive methyl radical from the photoinitiator, which then attacks double bonds in the PEGDA and initiates a chain reaction (Mellott et al., 2001).

Example 2

Pretreatment of Glass Slides

Clean 2" circular borosilicate glass wafers (Erie Scientific, Portsmouth, N.H.) were treated with a 2% v/v solution of 3-(trimethoxysilyl) propyl methacrylate (Aldrich, Milwaukee, Wis.) in 95% ethanol (pH 5 with acetic acid) for 2 minutes, rinsed with 100% ethanol, and then baked at 110 C, leaving free methacrylate groups on the glass to react with the PEGDA during UV exposure.

Example 3

Photopatterning of Hydrogel

An apparatus was designed for photopatterning of the PEGDA hydrogels (FIG. 1). Prepolymer solution was injected into a chamber with a Teflon base and a pretreated 2 inch borosilicate glass wafer on top to allow penetration of the UV light. The height of the chamber was determined by the thickness of the silicone spacer (100 micron) separating the glass and Teflon.

Light patterning was made possible by creating an emulsion mask that allows UV light to pass through only desired regions. Masks were drawn using Corel Draw 9.0 and printed using a commercial Linotronic-Hercules 3300 dpi high-resolution line printer. The mask was placed on top of the glass wafer of the polymer chamber, and was pressed flat to the wafer by a glass slide. All layers were held together by caliper screws that also controlled the exact height of the chamber. Upon hydrogel crosslinking (365 nm light, 10 mW/cm$^2$ the remaining uncrosslinked prepolymer solution and cells were washed away with HEPES buffered saline solution. To add another cell type, the mask was changed and the next prepolymer/cell solution was injected and exposed to UV light. For additional hydrogel layers, a thicker spacer was also used.

Example 4

Cell culture and viability assays in the presence of photopolymerizing agents. HepG2 cells (American Type Culture Collection, Manassas, Va.) were cultured in 175 cm$^2$ flasks (Fisher, Springfield, N.J.) and were passaged preconfluency no more than 13 times. The cells were maintained in minimal essential medium (MEM; Gibco, Grand Island, N.Y.) supplemented with 5% fetal bovine serum, 100 ug/mL penicillin, and 100 ug/mL streptomycin and incubated at 5% $CO_2$ and 37° C. The cells to be incorporated into hydrogels were added to the prepolymer solution containing initiator and were mixed gently prior to UV exposure.

In order to explore the effects of photoinitiator and UV exposure on cell death, individual components were tested in HepG2 cultures. $3.0 \times 10^5$ cells were seeded in six-well culture dishes and allowed to proliferate until near confluency. A solution of 300 mg/mL of 2,2-dimethyl-2-phenyl-acetophenone (Aldrich) in 1-vinyl-2-pyrrolidinone (Sigma) was added to MEM in concentrations of 0, 3, 5, and 10 ul/ml. The six-well plates were then rinsed with fresh MEM media to remove any dead or non-adherent cells, and 1 mi of the media containing initiator were added to each well. Cells were then exposed to 0, 30, or 60 seconds of UV light (365 nm, 10 mW/cm$^2$) and allowed to incubate at 37° C. for 2 hours. The effects of the initiator solvent 1-vinyl-2-pyrrolidinone alone were also tested in the same manner. This incubation time was considered to be an over estimate of exposure time during photopolymerization protocols. Cell viability was measured by an Mi viability assay, which forms a purple precipitate by cleavage of the tetrazolium ring by mitochondrial dehydrogenase enzymes. The MTT (3-(4,5-dimethylthiazol-2-yl)-2,5-diphenyltetrazolium bromide; Sigma, St. Louis, Mo.) was added to cells in medium without phenol red at a concentration of 0.5 mg/mL. After an incubation time of 3 hours, live cells had formed a purple precipitate, which was dissolved in a DMSO/Isopropanol solution. The absorbance was measured at 570 nm with a SpectraMax Plus spectrophotometer (Molecular Devices, Sunnyvale, Calif.). Viability was also viewed qualitatively using the Calcein AM and ethidium homodimer live/dead fluorescent stains (Molecular Probes, Eugene, Oreg.).

UV exposure did not significantly reduce cell viability in the absence of photoinitiator over the range of doses we studied. In contrast, the acetophenone (photoinitiator) solution did prove to have toxic effects for HepG2 cells at amounts greater than 0.9 g/ml. In addition, the combination of acetophenone and UV exposure further increased the toxicity of the initiator, presumably by producing harmful free radicals. It should be noted that these experiments were conducted in the absence of the polymer PEGDA, which would serve as an additional sink for free radicals during photocrosslinking. Therefore, the conditions induced in our viability study were an overestimation of the toxic effect seen by live cells photoencapsulated in this hydrogel system. In addition, the initiator solvent 1-vinyl-2-pyrrolidinone alone was not found to be toxic to cells in amounts used for photocrosslinking. The distribution of cell viability within the hydrogel network was assessed microscopically by both an MTT stain and a fluorescent live/dead stain. No significant spatial variation in cell viability was observed.

Example 5

Patterning Resolution

The effects of UV exposure time and photoinitiator concentration on resolution of hydrogel patterning were studied to characterize the limitations of the technique. Masks with line features of various widths were used to pattern hydrogel under different UV and initiator conditions. Images of features were recorded within minutes after UV exposure. Indistinct edges were seen in some cases, in particular for larger feature sizes. In such cases, the feature was measured from the outermost part of the hydrogel. Results showed that large features (>200 microns) had greater fidelity than smaller features (<80 microns), which tended to result in hydrogel lines wider than the intended line width. This was the case for all UV exposure times and initiator concentrations tested. For the smaller features, increased UV exposure was shown to increase the width of hydrogel features and reduce patterning resolution. Unexpectedly, varying the amount of initiator did not affect the resolution of patterning (FIG. 4A). Thus, the smallest amount of initiator needed to achieve photocrosslinking can be used to reduce cell toxicity, without concern that resolution will be lost. Hydrogel feature sizes were compared to mask features both in relative percentage compared to the mask as well as by looking at the absolute change in line width. The absolute line width change was approximately 30 microns per edge for large feature sizes (300-500 microns) and 50 microns for smaller feature sizes (50-200 microns).

Example 6

Microscopy

Hydrogels and cells were observed and recorded using a Nikon Diaphot microscope equipped with a SPOT digital camera (SPOT Diagnostic Equipment, Sterling Heights, Mich.), and MetaMorph Image Analysis System (Universal Imaging, Westchester, Pa.) for digital image acquisition. Cells labeled with chloromethylfluorescein diacetate (CM-FDA, C-2925, Molecular Probes) and chloromethyl benzoylaminotetramethyl rhodamine (CMTMR, C-2927) were observed by fluorescence microscopy with ex/em: 492/517 and 541/565 nm. In some cases, Hoechst nuclear stain was used (Molecular Probes) and viewed using fluorescent microscopy. Hydrogel resolution was determined by measuring line width using phase contrast microscopy and comparing to the actual size of the mask features. Three measurements were made for each condition, using MetaMorph software.

Example 7

Hydrogel Microstructures Containing Living Cells

Figure 2:
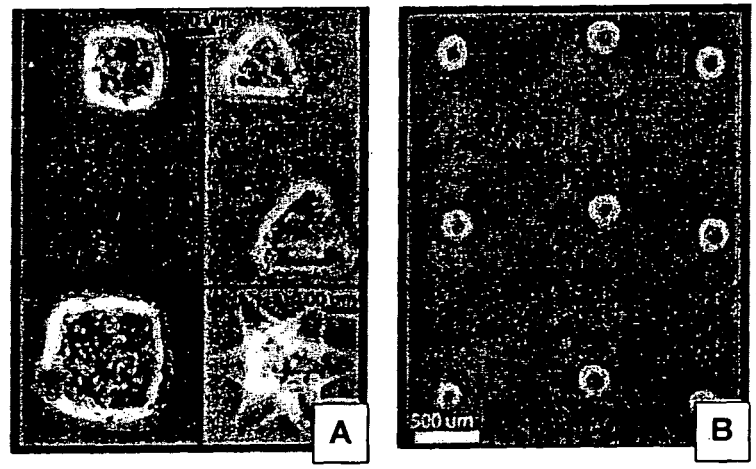
FIG. 2. Examples of hydrogel microstructures containing living cells. (A) Cells entrapped in PEGDA hydrogels patterned in various shapes (B) Phase microscopy of cellular array covalently linked to a glass substrate.

The fabricated hydrogels were photopatterned in various shapes, demonstrating the basic utility of the method disclosed herein to incorporate living mammalian cells in hydrogel microstructures of arbitrary form (FIG. 2A-B). Typical microstructures were on the order of 200 microns. The technique was extended to form a composite hydrogel structure that had two distinct cellular constituents in well-defined domains (FIG. 3B). This was achieved by photopatterning one cell type, rinsing away the uncrosslinked polymer and cells, addition of a second cell type in the bare regions followed by uniform exposure to UV light. This type of tissue structure cannot be achieved using other existing techniques.

A similar approach was utilized to photoimmobilize cells in hydrogel microstructures in an array format for applications in cell-based screening. Specifically, a first cell type was photopatterned, the remaining polymer and cells were washed away, a second cell type was introduced and exposure to UV light was conducted through a second mask (FIGS. 3C-D). By increasing the thickness of the spacer in the apparatus, multilayer hydrogel structures were formed. Sequential fabrication techniques of this genre are referred to as solid free form fabrication and are typically utilized for rapid prototyping. Herein, this approach to the fabrication of living tissues was extended. In the example, a mask of parallel lines was used for the first layer, then rotated and used in conjunction with a thicker spacer to create a second layer of hydrogel that is taller than the first (FIG. 3A, no cells). When different cell populations were incorporated into each layer, the result can be seen in FIG. 3B, in which cells are entrapped within horizontal lines in one layer, and cells are contained within the layer of vertical lines. Addition of a third layer resulted in an even more complex 3-dimensional structure (FIGS. 5C-D). This type of tissue structure has not been achieved using other techniques.

Example 8

Cell Viability in Hydrogel

Various cell types, including cell lines (3T3 fibroblasts, human hepatocytes) and primary cells (calf and adult bovine chondrocytes, rat hepatocytes) were released into suspension culture in appropriate media. Pelleted cells were then mixed with a photosensitive poly(ethylene glycol) (PEG)-based hydrogel solution previously characterized for chondrocyte immobilization, and introduced into the patterning chamber. High frequency AC voltage applied to the electrode array resulted in cell motion, with patterning typically complete within a few minutes. UV illumination solidified the prepolymer solution within minutes. The chamber was then opened and solid gels were transferred to sterile tissue culture wells with appropriate media (e.g. for chondrocyte culture, DMEM (Dulbecco's Modified Eagle's Medium, low glucose, e.g. Gibco 11885-084) supplemented with 10-20% FBS (fetal bovine serum), 0.1 mM non-essential amino acids, 10 mM HEPES, 2 mM L-glutamin, 0.4 mM L-proline was used. Optional additions include 25-100 ug/ml ascorbate to enhance biosynthetic activity, and antifungal/antibiotics (100 U/ml penicillin, 100 ug/ml streptomycin, 0.25 ug/ml amphotericin B).

At various time points up to several weeks, portions of cell-patterned gels were removed and probed for viability using fluorescent dyes (Live/Dead kit, Molecular Probes) or markers of differentiated cell function, e.g. sulfate GAG production for chondrocytes. Cells were found to remain viable and to express tissue specific markers for the duration of the experiment (8 weeks in unpatterned hydrogels, 4 weeks in patterned hydrogels).

Example 9

Screen for Biological Activity of Bioactive Compounds

A homogeneous or heterogeneous cell population is seeded into the biopolymer scaffold of the instant invention. A compound of interest, a putative drug, toxin or other bioactive compound, is added to the growth media of the bioreactor. Hepatocytes would be most commonly used in such an apparatus to study first pass effects. Hepatocytes for use in such an apparatus include primary cultures from human, pig or other appropriate source. Other hepatocytes-like cell lines can be used including immortalized primary cell lines, hepatocellular cell lines (hepatomas), adult stem-cell derived hepatocycles (i.e. from oral cells, bone marrow stem cells, mesenchymal stem cells), embryonic stem cells and fetal heptic cells. Alternatively, a mixture of compounds can be added to the bioreactor to test drug interactions. A manual high throughput assay can be envisioned by placing individual scaffolds into individual wells in a multiwell plate or by creating large numbers of cell clusters in a single or multiple biopolymer scaffolds. Alternatively, it may be done using an automated system such as that described by Griffith (U.S. Pat. No. 6,197,575 incorporated herein by reference). Cells are monitored under physiological conditions for response to the compounds tested by bioassay performed on the perfused fluid or by direct observation of the cells in the biopolymer. Cells can be monitored for signs of toxicity (e.g. change in metabolism or viability) or responses characteristic of prototypic toxins (e.g. apoptosis, upregulation of key pathways such as cytochrome P450 enzymes by activation of the SRX nuclear receptor). The activity of the compound may be detected in situ using an intra- or pericellular probe.

Compounds may be recovered from the growth media and assayed to determine if and how the compound was metabolized by the cell. The products of metabolism can reveal what enzymes were responsible for the processing of the compound. Thus it may be categorized into a class of molecules. Such information is useful in predicting drug interactions by determining if compounds are processed by the same mechanism.

Example 10

Protein Production or Biotransformation

Bioreactors containing the cells of interest can be assembled into a large scale reactor by methods well known to those skilled in the art. Cells may express an endogenous protein (e.g. antibodies from lymphocytes; insulin from β-islet cells) or they may be used to express heterologous proteins from nucleic acids transferred into the cell by any of a number of methods. Such a system is useful for the production of secreted proteins. Cells are patterned into the hydrogel. If required, factors are added or removed from the culture media to induce the production of protein (e.g. removal of tetracycline to de-repress a tetracycline promoter). Cells may be continuously perfused using a recirculating pump that pumps media through the chamber in which the bioreactors are held. The orientation of the perfusion may be essentially any orientation as the cells are adherent. The cells may be continuously perfused with fresh media or be maintained without perfusion. After protein expression, media is collected and proteins of interest are purified by any of a number of methods well known to those skilled in the art. As the cells are viable and maintain their state of differentiation in the bioreactor of the invention, the media may be changed upon depletion of nutrients for continuous protein production.

Biotransformation of compounds can be performed in a similar reactor. The compound is added to the growth media of the cells. After the allotted time, the media is collected and the compound is analyzed by HPLC or other methods well known to those skilled in the art.

Example 11

Enhanced Function of Rat Hepatocytes Encapsulated within Photopatterned Hydrogel Microstructures Compared with Unpatterned Hydrogels.

Figure 10:
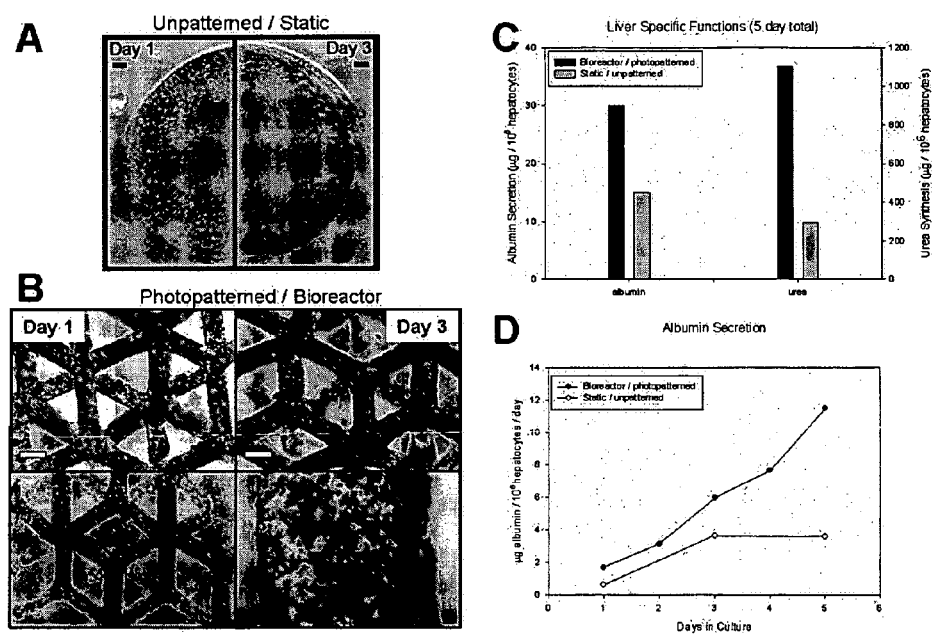
FIG. 10. Enhanced function of rat hepatocytes within photopatterned hydrogel microstructures compared with unpatterned hydrogels. A, B) Live, metabolically active hepatocytes, indicated by dark staining via MTT assay, are localized to the periphery of unpatterned, statically-cultured hydrogels (A). In contrast, hepatocytes encapsulated within photopatterned hydrogels and cultured in a perfusion bioreactor remain metabolically active throughout the construct, due to enhanced nutrient transport (B). Scale bars, 500 um. C) Liver specific functions are enhanced in photopatterned compared with unpatterned hepatocyte-laden hydrogels, using cumulative albumin and urea secretion as markers. D) Albumin secretion increases steadily over 5 days in perfused, photopatterned constructs but plateaus in static, unpatterned hydrogels.

Because hepatocytes are metabolically active and consume oxygen and nutrients, mass transport may be a limiting factor in hepatocyte-laden constructs. Live, metabolically active hepatocytes, indicated by dark staining via MTT assay, are localized to the periphery of an unpatterned, statically-cultured, 10 mm diameter hydrogel (FIG. 10A). To increase the construct surface area and thereby enhance mass transport, similar hepatocyte-laden hydrogels were photopatterned using the invention in a hexagonal pattern with spokes 500 um across (FIG. 10B). Hepatocytes encapsulated within these photopatterned hydrogels and cultured in a perfusion bioreactor remained metabolically active throughout the construct, due to enhanced nutrient transport. Liver specific functions were enhanced in the photopatterned constructs compared with unpatterned hydrogels, using cumulative albumin and urea secretion, normalized to cell number, as functional markers (FIG. 10C). Additionally, albumin secretion increased steadily over 5 days in perfused, photopatterned constructs, reaching 11.5 ug/10^6 cells/day by day 5, but plateaued after 3 days at ~3 ug/10^6 cells/day in static, unpatterned hydrogels.

Example 12

Control of Amount and Spatial Deposition of Sulfated Proteoglycans by DEP Electropatterned Chondrocytes.

Figure 11:
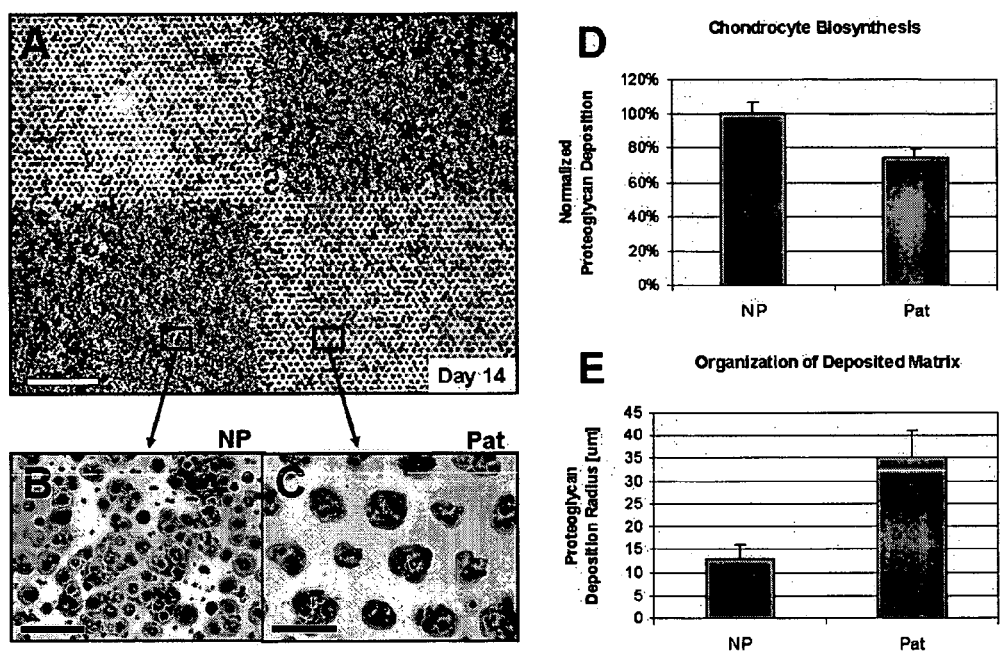
FIG. 11. Differential biosynthesis and deposition of matrix molecules by chondrocytes electropatterned within hydrogels. A) Low-magnification image of a 100 um thick hydrogel slab containing encapsulated bovine calf chondrocytes, either patterned in a hexagonal array of cell clusters spaced 100 um apart ("Pat", upper left and lower right quadrants) or non-patterned ("NP", upper right and lower left quadrants). Deposition of sulfated proteoglycans, a marker of differentiated chondrocyte function, is indicated at 14 days by dark staining via Alcian Blue dye. Scale bar, 1 mm. B, C) High magnification view of DEP electropatterned construct indicating the microscale organization of cells embedded within the hydrogel. Proteoglycan deposition occurs local to cells and forms patterns that reflect cell organization. Scale bars, 100 um. D) Chondrocytes patterned into clusters deposit less sulfated proteoglycan than unpatterned controls containing identical cells and cell density. E) Clustered chondrocytes deposit matrix molecules in distinct organization (C), producing dark-staining regions of larger diameter compared with unpatterned controls.

Bovine calf chondrocytes, isolated from femoral condyles by enzymatic digestion, were patterned into clusters of varying size (average 6-15 cells per cluster) within a 15×10 mm×100 um thick hydrogel slab using the invention. In two of four quadrants, clusters were patterned 100 um apart; elsewhere, the absence of electrodes resulted in non-patterned, randomly-organized cells (FIG. 11A). The cell source and spatial density were identical between the two geometries. Viability was similar at 1 d between patterned (95±1%) and unpatterned (93±1%) portions of individual gels and also at 3 d, demonstrating cytocompatible electric field and UV exposure conditions. To investigate the effect of cell organization on chondrocyte biosynthesis of matrix molecules, gels were stained at 14 days with Alcian Blue to selectively label sulfated proteoglycans deposited locally by the cells (FIG. 11B, C). The amount of deposited proteoglycans in each quadrant was quantified by extracting the Alcian Blue dye and reading absorbance values. Chondrocytes patterned into clusters deposited ~25% less sulfated proteoglycan than unpatterned controls containing identical cells and cell density (FIG. 11D). Additionally, the spatial pattern of proteoglycan deposition is controlled by chondrocyte organization. At 14 days, sulfated proteoglycan staining was localized to a hexagonal array of large spherical domains (radius R=35±6 μm) around patterned clusters (6.6±2.4 cells each), in contrast to unpatterned controls (R=13±3 μm, p<0.0001, FIG. 11E).

REFERENCES

A. Ashkin, *ASGSB Bull.* 4(a): 133-46 (1991)
S. F. Badylak, K. Park, N. Peppas, O. McCabe, and M. Yoder, *Exp. Hematol.* 29 (11), 1310-1318 (2001).
D. J. Beebe, J. S. Moore, J. M. Bauer, Y. Qing, R. H. Liu, C. Devadoss, and J. Byung-Ho, *Nature* 404(6778), 588-590 (2000).
S. N. Bhatia, U. J. Balls, M. L. Yarmush, and M. Toner, *FASEB Journal* 13 (14), 1883-1900 (1999).
S. J. Bryant and K. S. Anseth, *J. Biomed. Mater. Res.* 59(1), 63-72 (2002).
G. Chen, Y. Imanishi, and Y. Ito, *Langmuir* 14, 6610-6612 (1998).
N. Dubey, P. C. Letourneau and R. T. Tranquillo, *Biomaterials* 22 (10): 1065-75.
J. Elisseeff, W. Mcintosh, K. Anseth, S. Riley, P. Ragan, and R. Langer, *J. of Biomed Mat Res.* 51 (2), 164-171 (2000).
A. Folch, A. Ayon, O. Hurtado, M. A. Smith and M. Toner, *J. Biomech Eng.* 121(1): 28-34 (1999)
A. Folch, B. H. Jo, O. Hurtado, D. J. Beebe and M. Toner, *J Biomed Mater. Res.* 52 (2): 346-53 (2000)
A. S. Gobin and J. L. West, *FASEB Journal* 16 (7), 75 1-753 (2002).
L. G. Griffith, B. Wu, Mi. Cima, M. J. Powers, B. Chaignaud, and J. P. Vacanti, *Ann. N. Y. Acad. Sci.* 831, 382-397 (1997).
T. Heida, W. L. Rutten and E. Marani, *IEEE Trans Biomed. Eng.* 48(8), 921-930. (2001).
D. L. Hern and J. A. Hubbell, *J. Biomed. Mat Res.* 39 (2), 266-276 (1998).
J. Hodgson, *Nat Biotech.*, 19: 722-726 (2001).
R. Kapur, B. J. Spargo, M. S. Chen, J. M. Calvert, A. S. Rudolph, *J Biomed Mater Res.* 33: 205-16 (1996).
R. Landers and R. Mullhaupt, *Macrol. Mater. Eng.* 282, 17-21 (2000)
P. X. Ma and R. Zhang, *J. Biomed. Mater. Res.* 56 (4), 469-477 (2001).
B K. Mann, R H. Schmedlen, and J. L. West, *Biomaterials* 22 (5), 439-444 (2001).
B K. Mann, A S. Gobin, A T. Tsai, R. H. Schmedlen, and J. L. West, *Biomaterials* 22 (22), 3045-3051 (2001).
M. Matsue, R. Kageyama, D. T. Denhardt and M. Noda, *Bone* 20 (4) 329-34 (1997).
D. J. Odde and M. J. Renn, *Biotechnol Bioeng.* 67 (3): 312-8 (2000)
N A. Peppas, P. Bures, W. Leobandung, and H. Ichikawa, *Eur. J. Phaim. Biopharm.* 50(1), 27-46 (2000).
R. Pethig and G. H. Markx, *Tibtech.* 15: 426-432 (1997).
H. H. Vandenburgh, *Dev. Biol.* 93 (2): 438-43 (1982).
G. Vozzi, C. Flaim, A. Ahluwalia and S. Bhatia, *Biomaterials* 24: 2533-2540 (2003).
J. H. Ward, R. Bashir, and N. A. Pappas, *J. Biomed. Mater. Res.* 56 (3), 351-360 (2001).
T. H. Yang, H. Miyoshi, and N. Ohshima, *J. Biomed. Mater. Res.* 55 (3), 379-386 (2001).
T. Yu, E Chiellini, D. Schmaljohann, R. Solaro, and C. K. Ober, *Polymer Preprints* 41 (2), 1699-1700 (2000).

Although exemplary embodiments of the invention have been described above by way of examples, it will be understood by those skilled in the art that modifications may be made to the disclosed embodiments without departing from the scope of the invention, which is defined by the appended claims.

We claim:

1. A method for the microscale patterning of mammalian cells in 3-dimensions comprising:
    introducing a population of living mammalian cells in a patterning buffer into a chamber of a dielectrophoresis (DEP) apparatus, wherein the DEP apparatus comprises
    a positive electrode and
    a negative electrode, wherein one or both electrodes are micropatterned, a power source, wherein both electrodes are attached to the power source,
a bottom support comprising
a top surface and
a bottom surface,
a gasket sealed to the top surface of the bottom support to form the chamber, and
at least one opening in the chamber through which fluid and gases can be introduced into or purged from the chamber;
applying voltage from the power source for a time sufficient to generate a dielectrophoretic (DEP) field in the chamber which results from the one or both micropatterned electrodes, allowing for patterning at specific regions on the one or both micropatterned electrodes and retention of cells from the population of living cells;
removing the patterning buffer from the chamber;
introducing a mixture of photosensitive biopolymer and photopolymerizing agent into the chamber;
selectively photopolymerizing the biopolymer by shining light through a patterned mask on the top surface, bottom surface, or both surfaces, to provide patterned microstructures having a resolution of 30 to 50 microns; and
discontinuing the DEP field such that microscale patterning of the cells in 3-dimensions is achieved.

2. The method of claim 1, wherein at least the bottom support is transparent.

3. The method of claim 1, wherein the bottom support is a glass slide.

4. The method of claim 1, wherein at least one of the positive and negative electrodes is transparent.

5. The method of claim 4, wherein the one or both electrodes are micropatterned in micropatterns having features ranging from 5 to 100 microns in width, spaced from 10 to 250 microns apart.

6. The method of claim 1, wherein the apparatus further comprises a top that sealably engages the gasket for enclosing the chamber.

7. The method of claim 1, wherein the biopolymer is a PEG hydrogel.

8. The method of claim 1, further comprising repeating the method at least one additional time to create an additional layer of polymerized biopolymer containing living cells.

9. The method of claim 1, wherein the one or both electrodes are micropatterned in micropatterns having features ranging from 5 to 100 microns in width, spaced from 10 to 250 microns apart.

10. The method of claim 1 wherein the positive electrode is a continuous or discontinuous micropatterned positive electrode and the negative electrode is a continuous negative electrode.

11. The method of claim 1 wherein the one or both micropatterned electrodes comprises a micropattern of conductive and insulating materials.

* * * * *